(12) United States Patent
Hubschwerlen et al.

(10) Patent No.: US 9,487,516 B2
(45) Date of Patent: Nov. 8, 2016

(54) ANTIBACTERIAL OXADIAZOLONE DERIVATIVES

(71) Applicant: Actelion Pharmaceuticals Ltd., Allschwil (CH)

(72) Inventors: Christian Hubschwerlen, Durmenach (FR); Georg Rueedi, Allschwil (CH); Cornelia Zumbrunn, Allschwil (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 0 days.

(21) Appl. No.: 14/760,096

(22) PCT Filed: Jan. 8, 2014

(86) PCT No.: PCT/IB2014/058123
§ 371 (c)(1),
(2) Date: Jul. 9, 2015

(87) PCT Pub. No.: WO2014/108836
PCT Pub. Date: Jul. 17, 2014

(65) Prior Publication Data
US 2015/0353547 A1    Dec. 10, 2015

(30) Foreign Application Priority Data

Jan. 9, 2013 (EP) .................................. 13150707
Mar. 14, 2013 (EP) .................................. 13159274

(51) Int. Cl.
| | | |
|---|---|---|
| *A61K 31/4245* | (2006.01) | |
| *C07D 471/06* | (2006.01) | |
| *A61K 31/4375* | (2006.01) | |
| *C07D 471/16* | (2006.01) | |
| *C07D 487/06* | (2006.01) | |
| *C07D 519/00* | (2006.01) | |

(52) U.S. Cl.
CPC ......... *C07D 471/06* (2013.01); *A61K 31/4245* (2013.01); *A61K 31/4375* (2013.01); *C07D 471/16* (2013.01); *C07D 487/06* (2013.01); *C07D 519/00* (2013.01)

(58) Field of Classification Search
CPC ..................... A61K 31/4375; A61K 31/4245; C07D 471/06; C07D 471/16
USPC ........ 514/224, 255.5; 544/344, 345; 546/81, 546/82
See application file for complete search history.

(56) References Cited

FOREIGN PATENT DOCUMENTS

WO    WO 2010041194 A1 *  4/2010 ........... C07D 471/06

\* cited by examiner

Primary Examiner — Kamal Saeed
Assistant Examiner — Janet L Coppins
(74) Attorney, Agent, or Firm — Arent Fox LLP

(57) ABSTRACT

The invention relates to antibacterial compounds of formula I

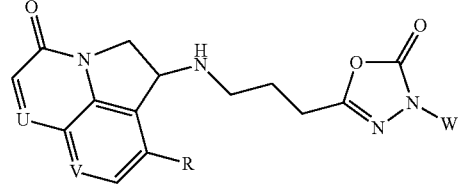

wherein
U represents CH or N;
V represents CH or N, provided that at least one of U and V does not represent N;
R represents H, halogen, methyl, methoxy, cyano or ethynyl;
either W represents a phenyl group substituted in para position with $(C_1-C_3)$alkyl, $(C_1-C_3)$alkoxy or $(C_1-C_3)$thioalkoxy and optionally in meta position with halogen, or W is a group having one of the formulae $W^1$ and $W^2$ below

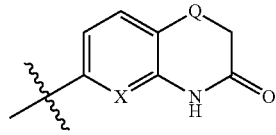

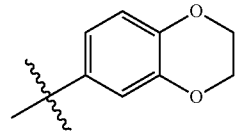

wherein
Q is O or S and
X is CH or N;
and salts of such compounds.

16 Claims, No Drawings

ANTIBACTERIAL OXADIAZOLONE DERIVATIVES

CROSS-REFERENCE TO RELATED APPLICATIONS

This application is the U.S. National Phase of International Patent Application No. PCT/IB2014/058123, filed Jan. 8, 2014, which claims the benefit of priorities to European Patent Application No. EP 13150707.1, filed Jan. 9, 2013, and European Patent Application No. EP 13159274.3, filed Mar. 14, 2013, the contents of each are hereby incorporated by reference in their entireties.

The present invention concerns antibacterial oxadiazolone derivatives, pharmaceutical compositions containing them and uses of these compounds in the manufacture of medicaments for the treatment of bacterial infections. These compounds are useful antimicrobial agents effective against a variety of human and veterinary pathogens including among others Gram-positive and Gram-negative aerobic and anaerobic bacteria and mycobacteria.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., Enterobacteriacea and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- Enteroccocci are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Furthermore, the incidence of multi-drug-resistant Gram-negative strains such as Enterobacteriacae and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome these multidrug-resistant bacilli.

In addition, microorganisms that are causing persistent infections are increasingly being recognized as causative agents or cofactors of severe chronic diseases like peptic ulcers or heart diseases.

WO 2012/041194 describes antibacterial compounds of formula (A1)

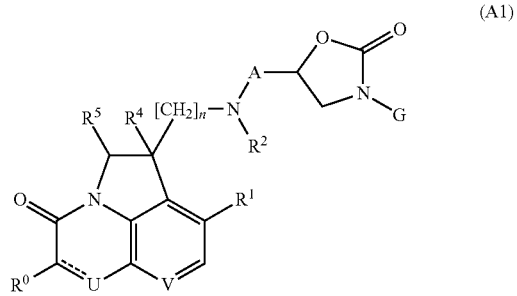

wherein
"-----" is (notably) a bond;
$R^0$ represents (notably) H;
$R^1$ represents (notably) halogen;
U represents CH or N when "-----" is a bond;
V represents (notably) CH;
$R^2$ represents (notably) H;
$R^4$ represents (notably) H;
$R^5$ represents (notably) H;
A represents (notably) —$(CH_2)_p$—;
G represents a phenyl group which is substituted once or twice in the meta and/or para position(s) by substituents selected independently from $(C_1$-$C_4)$alkyl, $(C_1$-$C_3)$alkoxy and a halogen, whereby a $(C_1$-$C_3)$alkoxy substituent is preferably a straight chain $(C_1$-$C_3)$alkoxy and in para position, or G is a group having one of the formulae $G^1$ and $G^2$ below

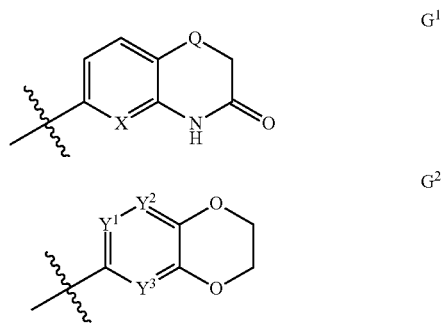

wherein
Q is O or S and X is CH or N; and
$Y^1$, $Y^2$ and $Y^3$ can notably each represent CH; and
n is 0, 1 or 2 when A represents —$(CH_2)_p$—, p being 1, 2, 3 or 4, with the proviso that the sum of n and p is then 2, 3 or 4.

An article by Mallur et al (*Il Farmaco* (2000), 55(1), 65-67) discloses notably compounds of formula (A2)

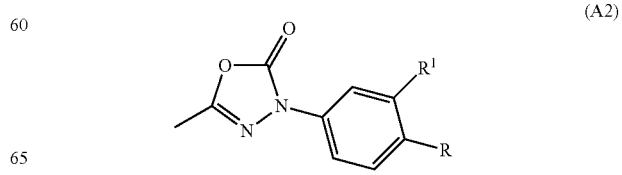

wherein
R represents H, Br or Cl and R¹ represents H; or
R represents H and R¹ represents Cl or methyl; or
R represents methyl and R¹ represents H, Cl or methyl; or also
R represents Cl and R¹ represents F.

However, among all the compounds of formula (A2), only the compounds wherein R represents Br or Cl and R¹ represents H, or R represents H and R¹ represents Cl showed, against either *Escherichia coli* or *Pseudomonas pyocyanous* bacteria, a growth inhibition activity equivalent to that of norfloxacin; the compound wherein R represents Cl and R¹ represents F showed a growth inhibition activity equivalent to that of norfloxacin against both *Escherichia coli* and *Pseudomonas pyocyanous* bacteria.

The instant invention provides new antibacterial compounds based on a oxadiazolone motif, namely the compounds of formula I described herein.

Various embodiments of the invention are presented hereafter:

1) The invention relates to compounds of formula I

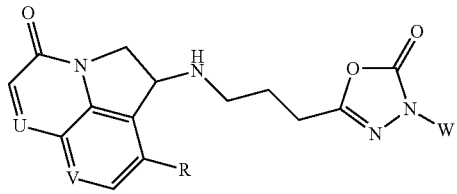

I wherein
U represents CH or N;
V represents CH or N, provided that at least one of U and V does not represent N;
R represents H, halogen, methyl, methoxy, cyano or ethynyl;
either W represents a phenyl group substituted in para position with $(C_1-C_3)$alkyl, $(C_1-C_3)$alkoxy or $(C_1-C_3)$thioalkoxy and optionally in meta position with halogen (preferably fluorine), or W is a group having one of the formulae W¹ and W² below

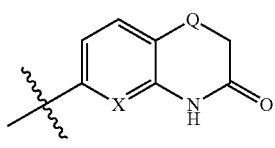

W¹

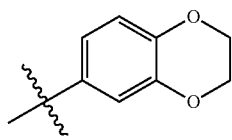

W² wherein
Q is O or S and
X is CH or N;
and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "$(C_1-C_x)$alkyl" (x being an integer) refers to a straight or branched chain alkyl group containing 1 to x carbon atoms. For example, a $(C_1-C_3)$alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl. Most preferred is methyl.

The term "alkoxy", used alone or in combination, refers to a straight or branched chain alkoxy group containing from one to four carbon atoms. The term "$(C_x-C_y)$alkoxy" (x and y each being an integer) refers to an alkoxy group as defined before containing x to y carbon atoms. For example, a $(C_1-C_3)$alkoxy group contains from one to three carbon atoms. Representative examples of alkoxy groups include methoxy, ethoxy, n-propoxy and iso-propoxy. Preferred are methoxy and ethoxy. Most preferred is methoxy.

The term "thioalkoxy", used alone or in combination, refers to an alkoxy group as defined before wherein the oxygen atom has been replaced by a sulphur atom. Apart from the sulphur atom, a thioalkoxy group thus includes a straight or branched chain alkyl containing from one to four carbon atoms. The term "$(C_x-C_y)$thioalkoxy" (x and y each being an integer) refers to a thioalkoxy group as defined before containing x to y carbon atoms. For example, a $(C_1-C_3)$thioalkoxy group contains from one to three carbon atoms. Representative examples of alkoxy groups include methylthio, ethylthio, n-propylthio and iso-propylthio. Preferred are methylthio and ethylthio. Most preferred is methylthio.

The term "halogen" refers to fluorine, chlorine, bromine or iodine, and preferably to fluorine or chlorine.

The term "quinolone-resistant", when used in this text, refers to a bacterial strain against which ciprofloxacin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006).

The term "methicillin-resistant", when used in this text, refers to a bacterial strain against which methicillin has a Minimal Inhibitory Concentration of at least 16 mg/l (said Minimal Inhibitory Concentration being measured with the standard method described in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006).

The term "pharmaceutically acceptable salts" refers to non-toxic, inorganic or organic acid and/or base addition salts. Reference can be made to "Salt selection for basic drugs", P. L. Gould, *Int. J. Pharm.* (1986), 33, 201-217.

In this text, a bond interrupted by a wavy line shows a point of attachment of the radical drawn to the rest of the molecule. For example, the radical drawn below

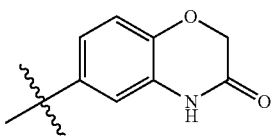 [SMILES: *c1ccc2c(c1)NC(=O)CO2]

is the 3-oxo-3,4-dihydro-2H-benzo[b][1,4]oxazin-6-yl group.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) A second embodiment of the invention relates to compounds of formula I according to embodiment 1) which are also compounds of formula $I_{E1}$

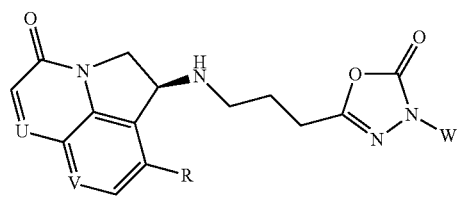

$I_{E1}$ wherein the absolute configuration of the asymmetric carbon of the tricyclic ring is as depicted in formula $I_{E1}$ [i.e. the absolute configuration of the asymmetric carbon of the tricyclic ring is (S)].

3) A third embodiment of the invention relates to compounds of formula I according to embodiment 1) which are also compounds of formula $I_{E2}$

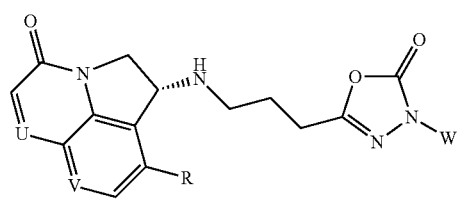

$I_{E2}$ wherein the absolute configuration of the asymmetric carbon of the tricyclic ring is as depicted in formula $I_{E2}$ [i.e. the absolute configuration of the asymmetric carbon of the tricyclic ring is (R)].

4) Preferably, the compounds of formula I as defined in one of embodiments 1) to 3) will be such that R represents H, fluorine, methyl, methoxy or cyano.

5) The invention notably relates to compounds of formula I according to embodiment 1) that are also compounds of formula $I_P$

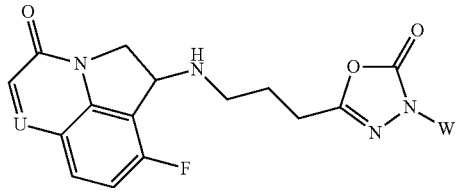

$I_P$ wherein

U represents CH or N;

either W represents a phenyl group substituted in para position with $(C_1-C_3)$alkyl, $(C_1-C_3)$alkoxy or $(C_1-C_3)$thioalkoxy and optionally in meta position with halogen (preferably fluorine), or W is a group having one of the formulae $W^1$ and $W^2$ below

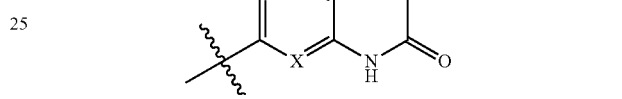

$W^1$

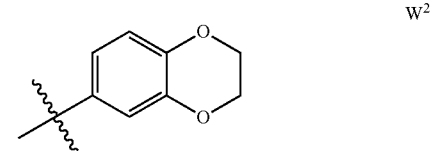

$W^2$ wherein

Q is O or S and

X is CH or N;

and to salts (in particular pharmaceutically acceptable salts) of compounds of formula $I_P$.

6) A further embodiment of the invention relates to compounds of formula $I_P$ according to embodiment 5) which are also compounds of formula $I_{PE1}$

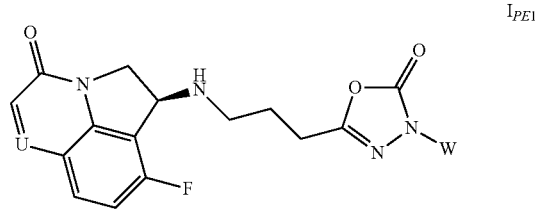

$I_{PE1}$ wherein the absolute configuration of the asymmetric carbon of the tricyclic ring is as depicted in formula $I_{PE1}$ [i.e. the absolute configuration of the asymmetric carbon of the tricyclic ring is (S)].

7) Yet a further embodiment of the invention relates to compounds of formula $I_P$ according to embodiment 5) which are also compounds of formula $I_{PE2}$

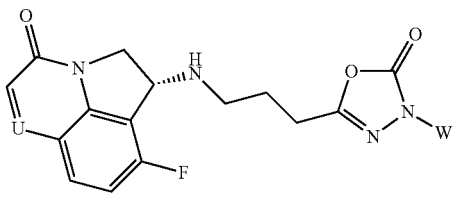

wherein the absolute configuration of the asymmetric carbon of the tricyclic ring is as depicted in formula $I_{PE2}$ [i.e. the absolute configuration of the asymmetric carbon of the tricyclic ring is (R)].

8) Preferably, the compounds of formula I as defined in one of embodiments 1) to 7) will be such that either W represents a phenyl group substituted in para position with ($C_2$-$C_3$)alkyl, ($C_1$-$C_3$)alkoxy or ($C_1$-$C_3$)thioalkoxy and optionally in meta position with halogen (preferably fluorine), or W is a group having one of the formulae $W^1$ and $W^2$ below

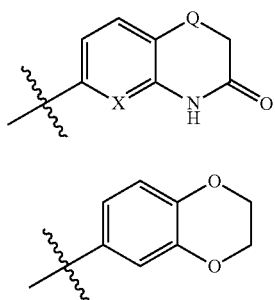

wherein
Q is O or S and
X is CH or N.

9) According to one main embodiment of this invention, the compounds of formula I as defined in one of embodiments 1) to 8) will be such that U represents CH and V, if present, represents CH.

10) One sub-embodiment of embodiment 9) relates to the compounds of formula I as defined in embodiment 9) wherein W is a group of formula $W^1$ as defined in embodiment 1).

11) Another sub-embodiment of embodiment 9) relates to the compounds of formula I as defined in embodiment 9) wherein W is a group of formula $W^2$ as defined in embodiment 1).

12) Yet another sub-embodiment of embodiment 9) relates to the compounds of formula I as defined in embodiment 9) wherein W represents a phenyl group substituted in para position with ($C_1$-$C_3$)alkyl, ($C_1$-$C_3$)alkoxy or ($C_1$-$C_3$)thioalkoxy and optionally in meta position with halogen (preferably fluorine).

13) According to another main embodiment of this invention, the compounds of formula I as defined in one of embodiments 1) to 4) will be such that each of U and V represents CH.

14) According to one variant of embodiment 13), the compounds of formula I as defined in embodiment 13) will be such that R represents fluorine.

15) According to another variant of embodiment 13), the compounds of formula I as defined in embodiment 13) will be such that R represents H.

16) According to yet another variant of embodiment 13), the compounds of formula I as defined in embodiment 13) will be such that R represents methyl or methoxy.

17) According to yet another variant of embodiment 13), the compounds of formula I as defined in embodiment 13) will be such that R represents cyano.

18) According to a further main embodiment of this invention, the compounds of formula I as defined in one of embodiments 1) to 4) will be such that U represents CH and V represents N.

19) According to one variant of embodiment 18), the compounds of formula I as defined in embodiment 18) will be such that R represents fluorine.

20) According to another variant of embodiment 18), the compounds of formula I as defined in embodiment 18) will be such that R represents H.

21) According to yet another variant of embodiment 18), the compounds of formula I as defined in embodiment 18) will be such that R represents methyl or methoxy.

22) According to yet another variant of embodiment 18), the compounds of formula I as defined in embodiment 18) will be such that R represents cyano.

23) According to another main embodiment of this invention, the compounds of formula I as defined in one of embodiments 1) to 8) will be such that U represents N.

24) One sub-embodiment of embodiment 23) relates to the compounds of formula I as defined in embodiment 23) wherein W is a group of formula $W^1$ as defined in embodiment 1).

25) Another sub-embodiment of embodiment 23) relates to the compounds of formula I as defined in embodiment 23) wherein W is a group of formula $W^2$ as defined in embodiment 1).

26) Yet another sub-embodiment of embodiment 23) relates to the compounds of formula I as defined in embodiment 23) wherein W represents a phenyl group substituted in para position with ($C_1$-$C_3$)alkyl, ($C_1$-$C_3$)alkoxy or ($C_1$-$C_3$)thioalkoxy and optionally in meta position with halogen (preferably fluorine).

27) Preferably, the compounds of formula I according to embodiment 26) will be such that W represents a phenyl group substituted in para position with ($C_2$-$C_3$)alkyl, ($C_1$-$C_3$)alkoxy or ($C_1$-$C_3$)thioalkoxy and optionally in meta position with halogen (preferably fluorine).

28) According to one variant of embodiment 23), the compounds of formula I as defined in embodiment 23) will be such that R represents fluorine.

29) According to another variant of embodiment 23), the compounds of formula I as defined in embodiment 23) will be such that R represents H.

30) According to yet another variant of embodiment 23), the compounds of formula I as defined in embodiment 23) will be such that R represents methyl or methoxy.

31) According to yet another variant of embodiment 23), the compounds of formula I as defined in embodiment 23) will be such that R represents cyano.

32) Preferably also, the compounds of formula I according to one of embodiments 28) to 31) will be such that W represents a phenyl group substituted in para position with ($C_2$-$C_3$)alkyl, ($C_1$-$C_3$)alkoxy or ($C_1$-$C_3$)thioalkoxy and optionally in meta position with halogen (preferably fluorine).

33) According to one preferred main variant of this invention, the compounds of formula I as defined in one of embodiments 1) to 8) will be such that W is a group of formula $W^1$ as defined in embodiment 1).

34) According to another main variant of this invention, the compounds of formula I as defined in one of embodiments 1) to 8) will be such that W is a group of formula $W^2$ as defined in embodiment 1).

35) According to yet another main variant of this invention, the compounds of formula I as defined in one of embodiments 1) to 8) will be such that W represents a phenyl group substituted in para position with $(C_1-C_3)$alkyl, $(C_1-C_3)$alkoxy or $(C_1-C_3)$thioalkoxy and optionally in meta position with halogen (preferably fluorine).

36) Preferably, the compounds of formula I as defined in embodiment 35) will be such that W represents a phenyl group substituted in para position with $(C_1-C_3)$alkyl, $(C_1-C_2)$alkoxy or $(C_1-C_2)$thioalkoxy and optionally in meta position with fluorine.

37) More preferably, the compounds of formula I according to embodiment 35) will be such that W represents a phenyl group substituted in para position with $(C_2-C_3)$alkyl, $(C_1-C_3)$alkoxy or $(C_1-C_3)$thioalkoxy and optionally in meta position with fluorine.

38) A preferred embodiment of this invention relates to the compounds of formula I according to embodiment 1), wherein:
U represents CH or N;
V represents CH or N, provided that at least one of U and V does not represent N;
R represents H, fluorine or cyano; and
either W represents a phenyl group substituted in para position with $(C_1-C_3)$alkyl, $(C_1-C_2)$thioalkoxy or $(C_1-C_2)$alkoxy and optionally in meta position with fluorine, or W is a group having one of the formulae $W^1$ and $W^2$ below

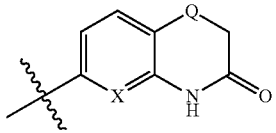

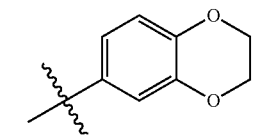

wherein
Q is O or S and
X is CH or N.

39) Preferably, the compounds of formula I according to embodiment 38) will be such that:
U represents CH or N;
V represents CH or N, provided that at least one of U and V does not represent N;
R represents H, fluorine or cyano; and
either W represents a phenyl group substituted in para position with $(C_2-C_3)$alkyl, $(C_1-C_2)$thioalkoxy or $(C_1-C_2)$alkoxy and optionally in meta position with fluorine, or W is a group having one of the formulae $W^1$ and $W^2$ below

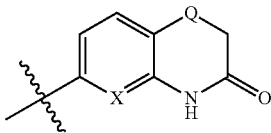

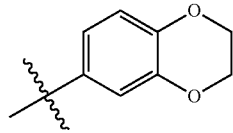

wherein
Q is O or S and
X is CH or N.

40) One sub-embodiment of embodiment 38) or 39) relates to the compounds of formula I as defined in embodiment 38) or 39) which have the same absolute configuration of the asymmetric carbon of the tricyclic ring as depicted in formula $I_{E1}$ of embodiment 2).

41) Another sub-embodiment of embodiment 38) or 39) relates to the compounds of formula I as defined in embodiment 38) or 39) which have the same absolute configuration of the asymmetric carbon of the tricyclic ring as depicted in formula $I_{E2}$ of embodiment 3).

42) In particular, the compounds of embodiments 38) to 41) will be such that V represents CH and R represents fluorine.

43) An even preferred embodiment of this invention relates to the compounds of formula I according to embodiment 1), wherein:
U represents CH or N;
V represents CH or N, provided that at least one of U and V does not represent N;
R represents fluorine or cyano; and
W is a group having the formula $W^1$ below

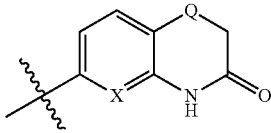

wherein
Q is O or S and
X is CH or N.

44) One sub-embodiment of embodiment 43) relates to the compounds of formula I as defined in embodiment 43) which have the same absolute configuration of the asymmetric carbon of the tricyclic ring as depicted in formula $I_{E1}$ of embodiment 2).

45) Another sub-embodiment of embodiment 43) relates to the compounds of formula I as defined in embodiment 43) which have the same absolute configuration of the asymmetric carbon of the tricyclic ring as depicted in formula $I_{E2}$ of embodiment 3).

46) In particular, the compounds of embodiments 43) to 45) will be such that V represents CH and R represents fluorine.

47) Another embodiment of this invention relates to compounds of formula I as defined in one of embodiments 1) to 46) as well as to isotopically labelled, especially ²H (deuterium) labelled compounds of formula I as defined in one of embodiments 1) to 46), which compounds are identical to the compounds of formula I as defined in one of embodiments 1) to 46) except that one or more atoms has or have each been replaced by an atom having the same atomic number but an atomic mass different from the atomic mass usually found in nature. Isotopically labelled, especially ²H (deuterium) labelled compounds of formula I and salts (in particular pharmaceutically acceptable salts) thereof are thus within the scope of the present invention. Substitution of hydrogen with the heavier isotope ²H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

48) Particularly preferred are the following compounds of formula I as defined in embodiment 1) or 5):
(S)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one;
(R)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[4-(4-isopropyl-phenyl)-5-oxo-4,5-dihydro-[1,3,4]oxadiazol-2-yl]-propylamino}-1,2-dihydro-pyrrolo[3,2,1-ij]quinolin-4-one;
(S)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one;
(R)-6-{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
(R)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one;
(R)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one;
(R)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one;
(R)-9-fluoro-1-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-1,2-dihydro-pyrrolo[3,2,1-ij]quinolin-4-one;
(S)-9-fluoro-1-{3-[5-oxo-4-(3-oxo-3,4-dihydro-2H-benzo[1,4]thiazin-6-yl)-4,5-dihydro-[1,3,4]oxadiazol-2-yl]-propylamino}-1,2-dihydro-pyrrolo[3,2,1-ij]quinolin-4-one;
(R)-7-fluoro-6-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-5,6-dihydro-pyrrolo[1,2,3-de]quinoxalin-3-one;

as well as the salts (in particular the pharmaceutically acceptable salts) thereof.

49) Also particularly preferred are the following compounds of formula I as defined in embodiment 1) or 5):
(R)-9-fluoro-1-{3-[5-oxo-4-(3-oxo-3,4-dihydro-2H-benzo[1,4]thiazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-benzo[1,4]thiazin-6-yl)-4,5-dihydro-[1,3,4]oxadiazol-2-yl]-propylamino}-5,6-dihydro-pyrrolo[1,2,3-de]quinoxalin-3-one;
(R)-7-fluoro-6-{3-[5-oxo-4-(3-oxo-3,4-dihydro-2H-benzo[1,4]thiazin-6-yl)-4,5-dihydro-[1,3,4]oxadiazol-2-yl]-propylamino}-5,6-dihydro-pyrrolo[1,2,3-de]quinoxalin-3-one;
(S)-1-{3-[4-(2,3-dihydro-benzo[1,4]dioxin-6-yl)-5-oxo-4,5-dihydro-[1,3,4]oxadiazol-2-yl]-propylamino}-9-fluoro-1,2-dihydro-pyrrolo[3,2,1-ij]quinolin-4-one;
(R)-1-{3-[4-(2,3-dihydro-benzo[1,4]dioxin-6-yl)-5-oxo-4,5-dihydro-[1,3,4]oxadiazol-2-yl]-propylamino}-9-fluoro-1,2-dihydro-pyrrolo[3,2,1-ij]quinolin-4-one;
(S)-6-{3-[4-(2,3-dihydro-benzo[1,4]dioxin-6-yl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-6-{3-[4-(2,3-dihydro-benzo[1,4]dioxin-6-yl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one;
(S)-1-{3-[4-(4-ethoxy-phenyl)-5-oxo-4,5-dihydro-[1,3,4]oxadiazol-2-yl]-propylamino}-9-fluoro-1,2-dihydro-pyrrolo[3,2,1-ij]quinolin-4-one;
(R)-1-{3-[4-(4-ethoxy-phenyl)-5-oxo-4,5-dihydro-[1,3,4]oxadiazol-2-yl]-propylamino}-9-fluoro-1,2-dihydro-pyrrolo[3,2,1-ij]quinolin-4-one;
(S)-6-{3-[4-(4-ethoxy-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;

(R)-6-{3-[4-(4-ethoxy-phenyl)-5-oxo-4,5-dihydro-[1,3,4]
oxadiazol-2-yl]-propylamino}-7-fluoro-5,6-dihydro-pyrrolo[1,2,3-de]quinoxalin-3-one;

(R)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one;

(S)-6-{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;

as well as the salts (in particular the pharmaceutically acceptable salts) thereof.

50) Besides, the following compounds of formula I as defined in embodiment 1) are also particularly preferred:

(S)-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;

(S)-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;

(R)-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;

(S)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propyl amino}-4,5-dihydro-pyrrolo[3,2,1-de][1,5]naphthyridin-7-one;

(R)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-4,5-dihydro-pyrrolo[3,2,1-de][1,5]naphthyridin-7-one;

(S)-9-methoxy-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;

(S)-9-methyl-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;

(S)-4-oxo-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-4H-pyrrolo[3,2,1-ij]quinoline-9-carbonitrile;

as well as the salts (in particular the pharmaceutically acceptable salts) thereof.

51) The invention further relates to the compounds of formula I as defined in embodiment 1) which are selected from the group consisting of the compounds listed in embodiment 48), the compounds listed in embodiment 49) and the compounds listed in embodiment 50). In particular, it also relates to the groups of compounds of formula I selected from the group consisting of the compounds listed in embodiment 48), the compounds listed in embodiment 49) and the compounds listed in embodiment 50), which groups of compounds furthermore correspond to one of embodiments 2) to 46), as well as to the salts (in particular the pharmaceutically acceptable salts) of such compounds. The invention moreover relates to any individual compound of formula I selected from the group consisting of the compounds listed in embodiment 48), the compounds listed in embodiment 49) and the compounds listed in embodiment 50), and to the salts (in particular the pharmaceutically acceptable salts) of such individual compound.

The compounds of formula I according to the invention, i.e. according to one of embodiments 1) to 51) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They may therefore be particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, Enterococcus casseliflavus, Staphylococcus epidermidis, Staphylococcus haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, S. pneumoniae, H. influenzae*, or *Chlamydia pneumoniae*; blood and tissue infections, including endocarditis and osteomyelitis, caused by *S. aureus, S. haemolyticus, E. faecalis, E. faecium, Enterococcus durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *S. aureus*, coagulase-negative staphylococci (i.e., *S. epidermidis, S. haemolyticus*, etc.), *S. pyogenes, Streptococcus agalactiae*, Streptococcal groups C—F (minute colony streptococci), viridans streptococci, *Corynebacterium minutissimum, Clostridium* spp., or *Bartonella henselae*; uncomplicated acute urinary tract infections related to infection by *S. aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, Mycobacterium leprae, Mycobacterium paratuberculosis, Mycobacterium kansasii*, or *Mycobacterium chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *H. pylori* or *C. pneumoniae*.

The preceding lists of infections and pathogens are to be interpreted merely as examples and in no way as limiting.

The compounds of formula I according to this invention, or the pharmaceutically acceptable salt thereof, may thus be used for the preparation of a medicament, and are suitable, for the prevention or treatment of a bacterial infection (notably for the prevention or treatment of a bacterial infection mediated by *Staphylococcus aureus* bacteria or *Acinetobacter baumanii* bacteria, especially for the prevention or treatment of a bacterial infection mediated by quinolone-resistant *Staphylococcus aureus* bacteria or *Acinetobacter baumanii* quinolone-resistant bacteria).

Accordingly, the compounds of formula I according to any one of embodiments 1) to 51) (and in particular the compounds of formula I according to embodiment 1) wherein W is a group $W^1$), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, Lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

The compounds of formula I according to any one of embodiments 1) to 51) (and in particular the compounds of formula I according to embodiment 1) wherein W is a group $W^1$), may further be useful for the preparation of a medicament, and are suitable, for the treatment of infections that are mediated by Gram negative bacteria (such as *Haemophilus influenzae, Moraxella catarrhalis, Escherichia coli, Klebsiella pneumoniae* and other Enterobacteriaceae, *Acinetobacter* spp. including *Acinetobacter baumanii, Pseudomonas aeruginosa, Stenotrophomonas maltophilia* and *Neisseria meningitidis*), notably by Gram negative bacteria selected from the group consisting of *Escherichia coli, Klebsiella pneumoniae, Acinetobacter baumanii, Pseudomonas aeruginosa, Moraxella catarrhalis, Stenotrophomonas maltophilia* and *Neisseria meningitidis*. In particular, compounds of formula I according to any one of embodiments 1) to 51) (and especially the compounds of formula I according to embodiment 1) wherein W is a group $W^1$) can be used for the preparation of a medicament, and are suitable, for the treatment of a bacterial infection mediated by *Acinetobacter baumanii* bacteria (especially quinolone-resistant *Acinetobacter baumanii* bacteria) or by *Moraxella catarrhalis* bacteria.

The compounds of formula I according to any one of embodiments 1) to 51) (and in particular the compounds of formula I according to embodiment 1) wherein W is a group $W^1$) may further be useful for the preparation of a medicament, and are suitable, for the treatment of infections that are mediated by Gram positive bacteria (such as *Staphylococcus aureus, Bacillus cereus, Bacillus anthracis, Clostridium difficile, Corynebacterium* spp. and *Propionibacterium acnes*), notably by Gram positive bacteria selected from the group consisting of *Bacillus cereus, Bacillus anthracis, Clostridium difficile* and *Propionibacterium acnes*. In particular, compounds of formula I according to any one of embodiments 1) to 51) can be used for the preparation of a medicament, and are suitable, for the treatment of a bacterial infection mediated by *Staphylococcus aureus* bacteria (especially quinolone-resistant *Staphylococcus aureus* bacteria).

The compounds of formula I according to any one of embodiments 1) to 51) may further be useful for the preparation of a medicament, and are suitable, for the treatment of protozoal infections caused by *Plasmodium* malaria, *Plasmodium falciparum, Toxoplasma gondii, Pneumocystis carinii, Trypanosoma brucei* and *Leishmania* spp.

The compounds of formula I according to this invention, or the pharmaceutically acceptable salt thereof, may moreover be used for the preparation of a medicament, and are suitable, for the prevention or treatment (and especially the treatment) of infections caused by biothreat bacterial pathogens as listed by the US Center for Disease Control (the list of such biothreat bacterial pathogens can be found at the web page http://www.selectagents.gov/Select%20Agents%20and%20Toxins%20List.html), and in particular by pathogens selected from the group consisting of *Bacillus anthracis* (anthrax), *Clostridium botulinum, Yersinia pestis, Francisella tularensis* (tularemia), *Burkholderia pseudomallei* and *Burkholderia mallei*.

One aspect of this invention therefore relates to the use of a compound of formula I according to one of embodiments 1) to 51) (and in particular to the use of a compound of formula I according to embodiment 1) wherein W is a group $W^1$), or of a pharmaceutically acceptable salt thereof, for the manufacture of a medicament for the prevention or treatment of a bacterial infection (in particular one of the previously mentioned infections mediated by Gram negative bacteria or one of the previously mentioned infections mediated by Gram positive bacteria). Another aspect of this invention relates to a compound of formula I according to one of embodiments 1) to 51) (and in particular to a compound of formula I according to embodiment 1) wherein W is a group $W^1$), or a pharmaceutically acceptable salt thereof, for the prevention or treatment of a bacterial infection (in particular for the prevention or treatment of one of the previously mentioned infections mediated by Gram negative bacteria or of one of the previously mentioned infections mediated by Gram positive bacteria). Yet another aspect of this invention relates to a compound of formula I according to one of embodiments 1) to 51) (and in particular a compound of formula I according to embodiment 1) wherein W is a group $W^1$), or a pharmaceutically acceptable salt thereof, as a medicament. Yet a further aspect of this invention relates to a pharmaceutical composition containing, as active principle, a compound of formula I according to one of embodiments 1) to 51) (and in particular a compound of formula I according to embodiment 1) wherein W is a group $W^1$), or a pharmaceutically acceptable salt thereof, and at least one therapeutically inert excipient.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I, $I_{E1}$, $I_{E2}$, $I_P$, $I_{PE1}$ or $I_{PE2}$.

Any reference to a compound of formula I, $I_{E1}$, $I_{E2}$, $I_P$, $I_{PE1}$ or $I_{PE2}$ in this text is to be understood as referring also to the salts (and especially the pharmaceutically acceptable salts) of such compounds, as appropriate and expedient.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The compounds of formula I and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection in a patient, comprising the administration to said patient of a pharmaceutically active amount of a compound of formula I according to one of embodiments 1) to 51) or a pharmaceutically acceptable salt thereof. Accordingly, the invention provides a method for the prevention or the treatment of a bacterial infection mediated by Gram negative bacteria (in particular a bacterial infection mediated by *Acinetobacter baumanii* bacteria, and especially by quinolone-resistant *Acinetobacter baumanii* bacteria) in a patient, comprising the administration to said patient of a pharmaceutically active amount of a compound of formula I according to one of embodiments 1) to 51) (and in particular of a compound of formula I according to embodiment 1) wherein W is a group $W^1$) or a pharmaceutically acceptable salt thereof. The invention further provides a method for the prevention or the treatment of a bacterial infection mediated by Gram positive bacteria (in particular a bacterial infection mediated by *Staphylococcus aureus* bacteria, especially by quinolone-resistant *Staphylococcus aureus* bacteria) in a patient, comprising the administration to said patient of a pharmaceutically active amount of a compound of formula I according to one of embodiments 1) to 51) (in particular of a compound of formula I according to embodiment 1) wherein W is a group $W^1$) or a pharmaceutically acceptable salt thereof.

Moreover, the compounds of formula I according to this invention may also be used for cleaning purposes, e.g. to remove pathogenic microbes and bacteria from surgical instruments, catheters and artificial implants or to make a room or an area aseptic. For such purposes, the compounds of formula I could be contained in a solution or in a spray formulation.

This invention, thus, relates to the compounds of formula I as defined in embodiment 1), or further limited under consideration of their respective dependencies by the characteristics of any one of embodiments 2) to 51), and to pharmaceutically acceptable salts thereof. It relates furthermore to the use of such compounds as medicaments, especially for the prevention or treatment of a bacterial infection, in particular for the prevention or treatment of a bacterial infection mediated by Gram positive bacteria (in particular a bacterial infection mediated by *Staphylococcus aureus* bacteria, especially by quinolone-resistant *Staphylococcus aureus* bacteria) or for the prevention or treatment of a bacterial infection mediated by Gram negative bacteria (in particular a bacterial infection mediated by *Acinetobacter baumanii* bacteria, and especially by quinolone-resistant *Acinetobacter baumanii* bacteria), and notably for the prevention or treatment of a bacterial infection mediated by quinolone-resistant *Staphylococcus aureus* or *Acinetobacter baumanii* bacteria. The following embodiments relating to the compounds of formula I according to embodiment 1) are thus possible and intended and herewith specifically disclosed in individualised form:

1, 2+1, 3+1, 4+1, 4+2+1, 4+3+1, 5+1, 6+1, 7+1, 8+1, 8+2+1, 8+3+1, 8+4+1, 8+4+2+1, 8+4+3+1, 8+5+1, 8+6+1, 8+7+1, 9+8+1, 9+8+2+1, 9+8+3+1, 9+8+4+1, 9+8+4+2+1, 9+8+4+3+1, 9+8+5+1, 9+8+6+1, 9+8+7+1, 10+9+8+1, 10+9+8+2+1, 10+9+8+3+1, 10+9+8+4+1, 10+9+8+4+2+1, 10+9+8+4+3+1, 10+9+8+5+1, 10+9+8+6+1, 10+9+8+7+1, 11+9+8+1, 11+9+8+2+1, 11+9+8+3+1, 11+9+8+4+1, 11+9+8+4+2+1, 11+9+8+4+3+1, 11+9+8+5+1, 11+9+8+6+1, 11+9+8+7+1, 12+9+8+1, 12+9+8+2+1, 12+9+8+3+1, 12+9+8+4+1, 12+9+8+4+2+1, 12+9+8+4+3+1, 12+9+8+5+1, 12+9+8+6+1, 12+9+8+7+1, 13+1, 13+2+1, 13+3+1, 13+4+1, 13+4+2+1, 13+4+3+1, 14+13+1, 14+13+2+1, 14+13+3+1, 14+13+4+1, 14+13+4+2+1, 14+13+4+3+1, 15+13+1, 15+13+2+1, 15+13+3+1, 15+13+4+1, 15+13+4+2+1, 15+13+4+3+1, 16+13+1, 16+13+2+1, 16+13+3+1, 16+13+4+1, 16+13+4+2+1, 16+13+4+3+1, 17+13+1, 17+13+2+1, 17+13+3+1, 17+13+4+1, 17+13+4+2+1, 17+13+4+3+1, 18+1, 18+2+1, 18+3+1, 18+4+1, 18+4+2+1, 18+4+3+1, 19+18+1, 19+18+2+1, 19+18+3+1, 19+18+4+1, 19+18+4+2+1, 19+18+4+3+1, 20+18+1, 20+18+2+1, 20+18+3+1, 20+18+4+1, 20+18+4+2+1, 20+18+4+3+1, 21+18+1, 21+18+2+1, 21+18+3+1, 21+18+4+1, 21+18+4+2+1, 21+18+4+3+1, 22+18+1, 22+18+2+1, 22+18+3+1, 22+18+4+1, 22+18+4+2+1, 22+18+4+3+1, 23+1, 23+2+1, 23+3+1, 23+4+1, 23+4+2+1, 23+4+3+1, 23+5+1, 23+6+1, 23+7+1, 23+8+1, 23+8+2+1, 23+8+3+1, 23+8+4+1, 23+8+4+2+1, 23+8+4+3+1, 23+8+5+1, 23+8+6+1, 23+8+7+1, 24+23+1, 24+23+2+1, 24+23+3+1, 24+23+4+1, 24+23+4+2+1, 24+23+4+3+1, 24+23+5+1, 24+23+6+1, 24+23+7+1, 24+23+8+1, 24+23+8+2+1, 24+23+8+3+1, 24+23+8+4+1, 24+23+8+4+2+1, 24+23+8+4+3+1, 24+23+8+5+1, 24+23+8+6+1, 24+23+8+7+1, 25+23+1, 25+23+2+1, 25+23+3+1, 25+23+4+1, 25+23+4+2+1, 25+23+4+3+1, 25+23+5+1, 25+23+6+1, 25+23+7+1, 25+23+8+1, 25+23+8+2+1, 25+23+8+3+1, 25+23+8+4+1, 25+23+8+4+2+1, 25+23+8+4+3+1, 25+23+8+5+1, 25+23+8+6+1, 25+23+8+7+1, 26+23+1, 26+23+2+1, 26+23+3+1, 26+23+4+1, 26+23+4+2+1, 26+23+4+3+1, 26+23+5+1, 26+23+6+1, 26+23+7+1, 26+23+8+1, 26+23+8+2+1, 26+23+8+3+1, 26+23+8+4+1, 26+23+8+4+2+1, 26+23+8+4+3+1, 26+23+8+5+1, 26+23+8+6+1, 26+23+8+7+1, 27+26+23+1, 27+26+23+2+1, 27+26+23+3+1, 27+26+23+4+1, 27+26+23+4+2+1, 27+26+23+4+3+1, 27+26+23+5+1, 27+26+23+6+1, 27+26+23+7+1, 27+26+23+8+1, 27+26+23+8+2+1, 27+26+23+8+3+1, 27+26+23+8+4+1, 27+26+23+8+4+2+1, 27+26+23+8+4+3+1, 27+26+23+8+5+1, 27+26+23+8+6+1, 27+26+23+8+7+1, 28+23+1, 28+23+2+1, 28+23+3+1, 28+23+4+1, 28+23+4+2+1, 28+23+4+3+1, 28+23+5+1, 28+23+6+1, 28+23+7+1, 28+23+8+1, 28+23+8+2+1, 28+23+8+3+1, 28+23+8+4+1, 28+23+8+4+2+1, 28+23+8+4+3+1, 28+23+8+5+1, 28+23+8+6+1, 28+23+8+7+1, 29+23+1, 29+23+2+1, 29+23+3+1, 29+23+4+1, 29+23+4+2+1, 29+23+4+3+1, 29+23+5+1, 29+23+6+1, 29+23+7+1, 29+23+8+1, 29+23+8+2+1, 29+23+8+3+1, 29+23+8+4+1, 29+23+8+4+2+1, 29+23+8+4+3+1, 29+23+8+5+1, 29+23+8+6+1, 29+23+8+7+1, 30+23+1, 30+23+2+1, 30+23+3+1, 30+23+4+1, 30+23+4+2+1, 30+23+4+3+1, 30+23+5+1, 30+23+6+1, 30+23+7+1, 30+23+8+1, 30+23+8+2+1, 30+23+8+3+1, 30+23+8+4+1, 30+23+8+4+2+1, 30+23+8+4+3+1, 30+23+8+5+1, 30+23+8+6+1, 30+23+8+7+1, 31+23+1, 31+23+2+1, 31+23+3+1, 31+23+4+1, 31+23+4+2+1, 31+23+4+3+1, 31+23+5+1, 31+23+6+1, 31+23+7+1, 31+23+8+1, 31+23+8+2+1, 31+23+8+3+1, 31+23+8+4+1, 31+23+8+4+2+1, 31+23+8+4+3+1, 31+23+8+5+1, 31+23+8+6+1, 31+23+8+7+1, 32+28+23+1, 32+28+23+2+1, 32+28+23+3+1, 32+28+23+4+1, 32+28+23+4+2+1, 32+28+23+4+3+1, 32+28+23+5+1, 32+28+23+6+1, 32+28+23+7+1, 32+28+23+8+1, 32+28+23+8+2+1,

32+28+23+8+3+1, 32+28+23+8+4+1, 32+28+23+8+4+2+1, 32+28+23+8+4+3+1, 32+28+23+8+5+1, 32+28+23+8+6+1, 32+28+23+8+7+1, 32+29+23+1, 32+29+23+2+1, 32+29+23+3+1, 32+29+23+4+1, 32+29+23+4+2+1, 32+29+23+4+3+1, 32+29+23+5+1, 32+29+23+6+1, 32+29+23+7+1, 32+29+23+8+1, 32+29+23+8+2+1, 32+29+23+8+3+1, 32+29+23+8+4+1, 32+29+23+8+4+2+1, 32+29+23+8+4+3+1, 32+29+23+8+5+1, 32+29+23+8+6+1, 32+29+23+8+7+1, 32+30+23+1, 32+30+23+2+1, 32+30+23+3+1, 32+30+23+4+1, 32+30+23+4+2+1, 32+30+23+4+3+1, 32+30+23+5+1, 32+30+23+6+1, 32+30+23+7+1, 32+30+23+8+1, 32+30+23+8+2+1, 32+30+23+8+3+1, 32+30+23+8+4+1, 32+30+23+8+4+2+1, 32+30+23+8+4+3+1, 32+30+23+8+5+1, 32+30+23+8+6+1, 32+30+23+8+7+1, 32+31+23+1, 32+31+23+2+1, 32+31+23+3+1, 32+31+23+4+1, 32+31+23+4+2+1, 32+31+23+4+3+1, 32+31+23+5+1, 32+31+23+6+1, 32+31+23+7+1, 32+31+23+8+1, 32+31+23+8+2+1, 32+31+23+8+3+1, 32+31+23+8+4+1, 32+31+23+8+4+2+1, 32+31+23+8+4+3+1, 32+31+23+8+5+1, 32+31+23+8+6+1, 32+31+23+8+7+1, 33+1, 33+2+1, 33+3+1, 33+4+1, 33+4+2+1, 33+4+3+1, 33+5+1, 33+6+1, 33+7+1, 33+8+1, 33+8+2+1, 33+8+3+1, 33+8+4+1, 33+8+4+2+1, 33+8+4+3+1, 33+8+5+1, 33+8+6+1, 33+8+7+1, 34+1, 34+2+1, 34+3+1, 34+4+1, 34+4+2+1, 34+4+3+1, 34+5+1, 34+6+1, 34+7+1, 34+8+1, 34+8+2+1, 34+8+3+1, 34+8+4+1, 34+8+4+2+1, 34+8+4+3+1, 34+8+5+1, 34+8+6+1, 34+8+7+1, 35+1, 35+2+1, 35+3+1, 35+4+1, 35+4+2+1, 35+4+3+1, 35+5+1, 35+6+1, 35+7+1, 35+8+1, 35+8+2+1, 35+8+3+1, 35+8+4+1, 35+8+4+2+1, 35+8+4+3+1, 35+8+5+1, 35+8+6+1, 35+8+7+1, 36+35+1, 36+35+2+1, 36+35+3+1, 36+35+4+1, 36+35+4+2+1, 36+35+4+3+1, 36+35+5+1, 36+35+6+1, 36+35+7+1, 36+35+8+1, 36+35+8+2+1, 36+35+8+3+1, 36+35+8+4+1, 36+35+8+4+2+1, 36+35+8+4+3+1, 36+35+8+5+1, 36+35+8+6+1, 36+35+8+7+1, 37+35+1, 37+35+2+1, 37+35+3+1, 37+35+4+1, 37+35+4+2+1, 37+35+4+3+1, 37+35+5+1, 37+35+6+1, 37+35+7+1, 37+35+8+1, 37+35+8+2+1, 37+35+8+3+1, 37+35+8+4+1, 37+35+8+4+2+1, 37+35+8+4+3+1, 37+35+8+5+1, 37+35+8+6+1, 37+35+8+7+1, 38+1, 39+38+1, 40+38+1, 40+39+38+1, 42+38+1, 42+39+38+1, 42+40+38+1, 42+40+39+38+1, 42+41, 43+1, 44+43+1, 45+43+1, 46+43+1, 46+44+43+1, 46+45+43+1, 47+1, 47+2+1, 47+3+1, 47+4+1, 47+4+2+1, 47+4+3+1, 47+5+1, 47+6+1, 47+7+1, 47+8+1, 47+8+2+1, 47+8+3+1, 47+8+4+1, 47+8+4+2+1, 47+8+4+3+1, 47+8+5+1, 47+8+6+1, 47+8+7+1, 47+9+8+1, 47+9+8+2+1, 47+9+8+3+1, 47+9+8+4+1, 47+9+8+4+2+1, 47+9+8+4+3+1, 47+9+8+5+1, 47+9+8+6+1, 47+9+8+7+1, 47+10+9+8+1, 47+10+9+8+2+1, 47+10+9+8+3+1, 47+10+9+8+4+1, 47+10+9+8+4+2+1, 47+10+9+8+4+3+1, 47+10+9+8+5+1, 47+10+9+8+6+1, 47+10+9+8+7+1, 47+11+9+8+1, 47+11+9+8+2+1, 47+11+9+8+3+1, 47+11+9+8+4+1, 47+11+9+8+4+2+1, 47+11+9+8+4+3+1, 47+11+9+8+5+1, 47+11+9+8+6+1, 47+11+9+8+7+1, 47+12+9+8+1, 47+12+9+8+2+1, 47+12+9+8+3+1, 47+12+9+8+4+1, 47+12+9+8+4+2+1, 47+12+9+8+4+3+1, 47+12+9+8+5+1, 47+12+9+8+6+1, 47+12+9+8+7+1, 47+13+1, 47+13+2+1, 47+13+3+1, 47+13+4+1, 47+13+4+2+1, 47+13+4+3+1, 47+14+13+1, 47+14+13+2+1, 47+14+13+3+1, 47+14+13+4+1, 47+14+13+4+2+1, 47+14+13+4+3+1, 47+15+13+1, 47+15+13+2+1, 47+15+13+3+1, 47+15+13+4+1, 47+15+13+4+2+1, 47+15+13+4+3+1, 47+16+13+1, 47+16+13+2+1, 47+16+13+3+1, 47+16+13+4+1, 47+16+13+4+2+1, 47+16+13+4+3+1, 47+17+13+1, 47+17+13+2+1, 47+17+13+3+1, 47+17+13+4+1, 47+17+13+4+2+1, 47+17+13+4+3+1, 47+18+1, 47+18+2+1, 47+18+4+1, 47+18+4+2+1, 47+19+18+1, 47+19+18+2+1, 47+19+18+3+1, 47+19+18+4+1, 47+19+18+4+2+1, 47+19+18+4+3+1, 47+20+18+1, 47+20+18+2+1, 47+20+18+3+1, 47+20+18+4+1, 47+20+18+4+2+1, 47+20+18+4+3+1, 47+21+18+1, 47+21+18+2+1, 47+21+18+3+1, 47+21+18+4+1, 47+21+18+4+2+1, 47+21+18+4+3+1, 47+22+18+1, 47+22+18+2+1, 47+22+18+3+1, 47+22+18+4+1, 47+22+18+4+2+1, 47+22+18+4+3+1, 47+23+1, 47+23+2+1, 47+23+3+1, 47+23+4+1, 47+23+4+2+1, 47+23+4+3+1, 47+23+5+1, 47+23+6+1, 47+23+7+1, 47+23+8+1, 47+23+8+2+1, 47+23+8+3+1, 47+23+8+4+1, 47+23+8+4+2+1, 47+23+8+4+3+1, 47+23+8+5+1, 47+23+8+6+1, 47+23+8+7+1, 47+24+23+1, 47+24+23+2+1, 47+24+23+3+1, 47+24+23+4+1, 47+24+23+4+2+1, 47+24+23+4+3+1, 47+24+23+5+1, 47+24+23+6+1, 47+24+23+7+1, 47+24+23+8+1, 47+24+23+8+2+1, 47+24+23+8+3+1, 47+24+23+8+4+1, 47+24+23+8+4+2+1, 47+24+23+8+4+3+1, 47+24+23+8+5+1, 47+24+23+8+6+1, 47+24+23+8+7+1, 47+25+23+1, 47+25+23+2+1, 47+25+23+3+1, 47+25+23+4+1, 47+25+23+4+2+1, 47+25+23+4+3+1, 47+25+23+5+1, 47+25+23+6+1, 47+25+23+7+1, 47+25+23+8+1, 47+25+23+8+2+1, 47+25+23+8+3+1, 47+25+23+8+4+1, 47+25+23+8+4+2+1, 47+25+23+8+4+3+1, 47+25+23+8+5+1, 47+25+23+8+6+1, 47+25+23+8+7+1, 47+26+23+1, 47+26+23+2+1, 47+26+23+3+1, 47+26+23+4+1, 47+26+23+4+2+1, 47+26+23+4+3+1, 47+26+23+5+1, 47+26+23+6+1, 47+26+23+7+1, 47+26+23+8+1, 47+26+23+8+2+1, 47+26+23+8+3+1, 47+26+23+8+4+1, 47+26+23+8+4+2+1, 47+26+23+8+4+3+1, 47+26+23+8+5+1, 47+26+23+8+6+1, 47+26+23+8+7+1, 47+27+26+23+1, 47+27+26+23+2+1, 47+27+26+23+3+1, 47+27+26+23+4+1, 47+27+26+23+4+2+1, 47+27+26+23+4+3+1, 47+27+26+23+5+1, 47+27+26+23+6+1, 47+27+26+23+7+1, 47+27+26+23+8+1, 47+27+26+23+8+2+1, 47+27+26+23+8+3+1, 47+27+26+23+8+4+1, 47+27+26+23+8+4+2+1, 47+27+26+23+8+4+3+1, 47+27+26+23+8+5+1, 47+27+26+23+8+6+1, 47+27+26+23+8+7+1, 47+28+23+1, 47+28+23+2+1, 47+28+23+3+1, 47+28+23+4+1, 47+28+23+4+2+1, 47+28+23+4+3+1, 47+28+23+5+1, 47+28+23+6+1, 47+28+23+7+1, 47+28+23+8+1, 47+28+23+8+2+1, 47+28+23+8+3+1, 47+28+23+8+4+1, 47+28+23+8+4+2+1, 47+28+23+8+4+3+1, 47+28+23+8+5+1, 47+28+23+8+6+1, 47+28+23+8+7+1, 47+29+23+1, 47+29+23+2+1, 47+29+23+3+1, 47+29+23+4+1, 47+29+23+4+2+1, 47+29+23+4+3+1, 47+29+23+5+1, 47+29+23+6+1, 47+29+23+7+1, 47+29+23+8+1, 47+29+23+8+2+1, 47+29+23+8+3+1, 47+29+23+8+4+1, 47+29+23+8+4+2+1, 47+29+23+8+4+3+1, 47+29+23+8+5+1, 47+29+23+8+6+1, 47+29+23+8+7+1, 47+30+23+1, 47+30+23+2+1, 47+30+23+3+1, 47+30+23+4+1, 47+30+23+4+2+1, 47+30+23+4+3+1, 47+30+23+5+1, 47+30+23+6+1, 47+30+23+7+1, 47+30+23+8+1, 47+30+23+8+2+1, 47+30+23+8+3+1, 47+30+23+8+4+1, 47+30+23+8+4+2+1, 47+30+23+8+4+3+1, 47+30+23+8+5+1, 47+30+23+8+6+1, 47+30+23+8+7+1, 47+31+23+1, 47+31+23+2+1, 47+31+23+3+1, 47+31+23+4+1, 47+31+23+4+2+1, 47+31+23+4+3+1, 47+31+23+5+1, 47+31+23+6+1, 47+31+23+7+1, 47+31+23+8+1, 47+31+23+8+2+1, 47+31+23+8+3+1, 47+31+23+8+4+1, 47+31+23+8+4+2+1, 47+31+23+8+4+3+1, 47+31+23+8+5+1, 47+31+23+8+6+1, 47+31+23+8+7+1, 47+32+28+23+1, 47+32+28+23+2+1, 47+32+28+23+3+1, 47+32+28+23+4+1, 47+32+28+23+4+2+1, 47+32+28+23+4+3+1, 47+32+28+23+5+1, 47+32+28+23+6+1, 47+32+28+23+7+1, 47+32+28+23+8+1, 47+32+28+23+8+2+1, 47+32+28+23+8+3+1, 47+32+28+23+8+4+1, 47+32+28+23+8+4+2+1, 47+32+28+23+8+4+3+1, 47+32+28+23+8+5+1, 47+32+28+23+8+6+1, 47+32+28+23+8+7+1, 47+32+29+23+1, 47+32+29+23+2+1, 47+32+29+23+3+1, 47+32+29+23+4+1, 47+32+29+23+4+2+1, 47+32+29+23+4+3+1, 47+32+29+23+5+1, 47+32+29+23+6+1, 47+32+29+23+7+1, 47+32+29+23+8+1,

47+32+29+23+8+2+1, 47+32+29+23+8+3+1, 47+32+29+23+8+4+1, 47+32+29+23+8+4+2+1, 47+32+29+23+8+4+3+1, 47+32+29+23+8+5+1, 47+32+29+23+8+6+1, 47+32+29+23+8+7+1, 47+32+30+23+1, 47+32+30+23+2+1, 47+32+30+23+3+1, 47+32+30+23+4+1, 47+32+30+23+4+2+1, 47+32+30+23+4+3+1, 47+32+30+23+5+1, 47+32+30+23+6+1, 47+32+30+23+7+1, 47+32+30+23+8+1, 47+32+30+23+8+2+1, 47+32+30+23+8+3+1, 47+32+30+23+8+4+1, 47+32+30+23+8+4+2+1, 47+32+30+23+8+4+3+1, 47+32+30+23+8+5+1, 47+32+30+23+8+6+1, 47+32+30+23+8+7+1, 47+32+31+23+1, 47+32+31+23+2+1, 47+32+31+23+3+1, 47+32+31+23+4+1, 47+32+31+23+4+2+1, 47+32+31+23+4+3+1, 47+32+31+23+5+1, 47+32+31+23+6+1, 47+32+31+23+7+1, 47+32+31+23+8+1, 47+32+31+23+8+2+1, 47+32+31+23+8+3+1, 47+32+31+23+8+4+1, 47+32+31+23+8+4+2+1, 47+32+31+23+8+4+3+1, 47+32+31+23+8+5+1, 47+32+31+23+8+6+1, 47+32+31+23+8+7+1, 47+33+1, 47+33+2+1, 47+33+3+1, 47+33+4+1, 47+33+4+2+1, 47+33+4+3+1, 47+33+5+1, 47+33+6+1, 47+33+7+1, 47+33+8+1, 47+33+8+2+1, 47+33+8+3+1, 47+33+8+4+1, 47+33+8+4+2+1, 47+33+8+4+3+1, 47+33+8+5+1, 47+33+8+6+1, 47+33+8+7+1, 47+34+1, 47+34+2+1, 47+34+3+1, 47+34+4+1, 47+34+4+2+1, 47+34+4+3+1, 47+34+5+1, 47+34+6+1, 47+34+7+1, 47+34+8+1, 47+34+8+2+1, 47+34+8+3+1, 47+34+8+4+1, 47+34+8+4+2+1, 47+34+8+4+3+1, 47+34+8+5+1, 47+34+8+6+1, 47+34+8+7+1, 47+35+1, 47+35+2+1, 47+35+3+1, 47+35+4+1, 47+35+4+2+1, 47+35+4+3+1, 47+35+5+1, 47+35+6+1, 47+35+7+1, 47+35+8+1, 47+35+8+2+1, 47+35+8+3+1, 47+35+8+4+1, 47+35+8+4+2+1, 47+35+8+4+3+1, 47+35+8+5+1, 47+35+8+6+1, 47+35+8+7+1, 47+36+35+1, 47+36+35+2+1, 47+36+35+3+1, 47+36+35+4+1, 47+36+35+4+2+1, 47+36+35+4+3+1, 47+36+35+5+1, 47+36+35+6+1, 47+36+35+7+1, 47+36+35+8+1, 47+36+35+8+2+1, 47+36+35+8+3+1, 47+36+35+8+4+1, 47+36+35+8+4+2+1, 47+36+35+8+4+3+1, 47+36+35+8+5+1, 47+36+35+8+6+1, 47+36+35+8+7+1, 47+37+35+1, 47+37+35+2+1, 47+37+35+3+1, 47+37+35+4+1, 47+37+35+4+2+1, 47+37+35+4+3+1, 47+37+35+5+1, 47+37+35+6+1, 47+37+35+7+1, 47+37+35+8+1, 47+37+35+8+2+1, 47+37+35+8+3+1, 47+37+35+8+4+1, 47+37+35+8+4+2+1, 47+37+35+8+4+3+1, 47+37+35+8+5+1, 47+37+35+8+6+1, 47+37+35+8+7+1, 47+38+1, 47+39+38+1, 47+40+38+1, 47+40+39+38+1, 47+41, 47+42+38+1, 47+42+39+38+1, 47+42+40+38+1, 47+42+40+39+38+1, 47+42+41, 47+43+1, 47+44+43+1, 47+45+43+1, 47+46+43+1, 47+46+44+43+1, 47+46+45+43+1, 48+1, 48+5+1, 49+1, 49+5+1, 50+1, 51+1, 51+2+1, 51+3+1, 51+4+1, 51+4+2+1, 51+4+3+1, 51+5+1, 51+6+1, 51+7+1, 51+8+1, 51+8+2+1, 51+8+3+1, 51+8+4+1, 51+8+4+2+1, 51+8+4+3+1, 51+8+5+1, 51+8+6+1, 51+8+7+1, 51+9+8+1, 51+9+8+2+1, 51+9+8+3+1, 51+9+8+4+1, 51+9+8+4+2+1, 51+9+8+4+3+1, 51+9+8+5+1, 51+9+8+6+1, 51+9+8+7+1, 51+10+9+8+1, 51+10+9+8+2+1, 51+10+9+8+3+1, 51+10+9+8+4+1, 51+10+9+8+4+2+1, 51+10+9+8+4+3+1, 51+10+9+8+5+1, 51+10+9+8+6+1, 51+10+9+8+7+1, 51+11+9+8+1, 51+11+9+8+2+1, 51+11+9+8+3+1, 51+11+9+8+4+1, 51+11+9+8+4+2+1, 51+11+9+8+4+3+1, 51+11+9+8+5+1, 51+11+9+8+6+1, 51+11+9+8+7+1, 51+12+9+8+1, 51+12+9+8+2+1, 51+12+9+8+3+1, 51+12+9+8+4+1, 51+12+9+8+4+2+1, 51+12+9+8+4+3+1, 51+12+9+8+5+1, 51+12+9+8+6+1, 51+12+9+8+7+1, 51+13+1, 51+13+2+1, 51+13+3+1, 51+13+4+1, 51+13+4+2+1, 51+13+4+3+1, 51+14+13+1, 51+14+13+2+1, 51+14+13+3+1, 51+14+13+4+1, 51+14+13+4+2+1, 51+14+13+4+3+1, 51+15+13+1, 51+15+13+2+1, 51+15+13+3+1, 51+15+13+4+1, 51+15+13+4+2+1, 51+15+13+4+3+1, 51+16+13+1, 51+16+13+2+1, 51+16+13+3+1, 51+16+13+4+1, 51+16+13+4+2+1, 51+16+13+4+3+1, 51+17+13+1, 51+17+13+2+1, 51+17+13+3+1, 51+17+13+4+1, 51+17+13+4+2+1, 51+17+13+4+3+1, 51+18+1, 51+18+2+1, 51+18+3+1, 51+18+4+1, 51+18+4+2+1, 51+18+4+3+1, 51+19+18+1, 51+19+18+2+1, 51+19+18+3+1, 51+19+18+4+1, 51+19+18+4+2+1, 51+19+18+4+3+1, 51+20+18+1, 51+20+18+2+1, 51+20+18+3+1, 51+20+18+4+1, 51+20+18+4+2+1, 51+20+18+4+3+1, 51+21+18+1, 51+21+18+2+1, 51+21+18+3+1, 51+21+18+4+1, 51+21+18+4+2+1, 51+21+18+4+3+1, 51+22+18+1, 51+22+18+2+1, 51+22+18+3+1, 51+22+18+4+1, 51+22+18+4+2+1, 51+22+18+4+3+1, 51+23+1, 51+23+2+1, 51+23+3+1, 51+23+4+1, 51+23+4+2+1, 51+23+4+3+1, 51+23+5+1, 51+23+6+1, 51+23+7+1, 51+23+8+1, 51+23+8+2+1, 51+23+8+3+1, 51+23+8+4+1, 51+23+8+4+2+1, 51+23+8+4+3+1, 51+23+8+5+1, 51+23+8+6+1, 51+23+8+7+1, 51+24+23+1, 51+24+23+2+1, 51+24+23+3+1, 51+24+23+4+1, 51+24+23+4+2+1, 51+24+23+4+3+1, 51+24+23+5+1, 51+24+23+6+1, 51+24+23+7+1, 51+24+23+8+1, 51+24+23+8+2+1, 51+24+23+8+3+1, 51+24+23+8+4+1, 51+24+23+8+4+2+1, 51+24+23+8+4+3+1, 51+24+23+8+5+1, 51+24+23+8+6+1, 51+24+23+8+7+1, 51+25+23+1, 51+25+23+2+1, 51+25+23+3+1, 51+25+23+4+1, 51+25+23+4+2+1, 51+25+23+4+3+1, 51+25+23+5+1, 51+25+23+6+1, 51+25+23+7+1, 51+25+23+8+1, 51+25+23+8+2+1, 51+25+23+8+3+1, 51+25+23+8+4+1, 51+25+23+8+4+2+1, 51+25+23+8+4+3+1, 51+25+23+8+5+1, 51+25+23+8+6+1, 51+25+23+8+7+1, 51+26+23+1, 51+26+23+2+1, 51+26+23+3+1, 51+26+23+4+1, 51+26+23+4+2+1, 51+26+23+4+3+1, 51+26+23+5+1, 51+26+23+6+1, 51+26+23+7+1, 51+26+23+8+1, 51+26+23+8+2+1, 51+26+23+8+3+1, 51+26+23+8+4+1, 51+26+23+8+4+2+1, 51+26+23+8+4+3+1, 51+26+23+8+5+1, 51+26+23+8+6+1, 51+26+23+8+7+1, 51+27+26+23+1, 51+27+26+23+2+1, 51+27+26+23+3+1, 51+27+26+23+4+1, 51+27+26+23+4+2+1, 51+27+26+23+4+3+1, 51+27+26+23+5+1, 51+27+26+23+6+1, 51+27+26+23+7+1, 51+27+26+23+8+1, 51+27+26+23+8+2+1, 51+27+26+23+8+3+1, 51+27+26+23+8+4+1, 51+27+26+23+8+4+2+1, 51+27+26+23+8+4+3+1, 51+27+26+23+8+5+1, 51+27+26+23+8+6+1, 51+27+26+23+8+7+1, 51+28+23+1, 51+28+23+2+1, 51+28+23+3+1, 51+28+23+4+1, 51+28+23+4+2+1, 51+28+23+4+3+1, 51+28+23+5+1, 51+28+23+6+1, 51+28+23+7+1, 51+28+23+8+1, 51+28+23+8+2+1, 51+28+23+8+3+1, 51+28+23+8+4+1, 51+28+23+8+4+2+1, 51+28+23+8+4+3+1, 51+28+23+8+5+1, 51+28+23+8+6+1, 51+28+23+8+7+1, 51+29+23+1, 51+29+23+2+1, 51+29+23+3+1, 51+29+23+4+1, 51+29+23+4+2+1, 51+29+23+4+3+1, 51+29+23+5+1, 51+29+23+6+1, 51+29+23+7+1, 51+29+23+8+1, 51+29+23+8+2+1, 51+29+23+8+3+1, 51+29+23+8+4+1, 51+29+23+8+4+2+1, 51+29+23+8+4+3+1, 51+29+23+8+5+1, 51+29+23+8+6+1, 51+29+23+8+7+1, 51+30+23+1, 51+30+23+2+1, 51+30+23+3+1, 51+30+23+4+1, 51+30+23+4+2+1, 51+30+23+4+3+1, 51+30+23+5+1, 51+30+23+6+1, 51+30+23+7+1, 51+30+23+8+1, 51+30+23+8+2+1, 51+30+23+8+3+1, 51+30+23+8+4+1, 51+30+23+8+4+2+1, 51+30+23+8+4+3+1, 51+30+23+8+5+1, 51+30+23+8+6+1, 51+30+23+8+7+1, 51+31+23+1, 51+31+23+2+1, 51+31+23+3+1, 51+31+23+4+1, 51+31+23+4+2+1, 51+31+23+4+3+1, 51+31+23+5+1, 51+31+23+6+1, 51+31+23+7+1, 51+31+23+8+1, 51+31+23+8+2+1, 51+31+23+8+3+1, 51+31+23+8+4+1, 51+31+23+8+4+2+1, 51+31+23+8+4+3+1, 51+31+23+8+5+1, 51+31+23+8+6+1, 51+31+23+8+7+1, 51+32+28+23+1, 51+32+28+23+2+1, 51+32+28+23+3+1, 51+32+28+23+4+1, 51+32+28+23+4+2+1, 51+32+28+23+4+3+1, 51+32+28+23+5+1, 51+32+28+23+6+1, 51+32+28+23+7+1, 51+32+28+23+8+1, 51+32+28+23+8+2+1, 51+32+28+23+8+3+1, 51+32+28+

23+8+4+1, 51+32+28+23+8+4+2+1, 51+32+28+23+8+4+ 3+1, 51+32+28+23+8+5+1, 51+32+28+23+8+6+1, 51+32+ 28+23+8+7+1, 51+32+29+23+1, 51+32+29+23+2+1, 51+32+29+23+3+1, 51+32+29+23+4+1, 51+32+29+23+4+ 2+1, 51+32+29+23+4+3+1, 51+32+29+23+5+1, 51+32+ 29+23+6+1, 51+32+29+23+7+1, 51+32+29+23+8+1, 51+32+29+23+8+2+1, 51+32+29+23+8+3+1, 51+32+29+ 23+8+4+1, 51+32+29+23+8+4+2+1, 51+32+29+23+8+4+ 3+1, 51+32+29+23+8+5+1, 51+32+29+23+8+6+1, 51+32+ 29+23+8+7+1, 51+32+30+23+1, 51+32+30+23+2+1, 51+32+30+23+3+1, 51+32+30+23+4+1, 51+32+30+23+4+ 2+1, 51+32+30+23+4+3+1, 51+32+30+23+5+1, 51+32+ 30+23+6+1, 51+32+30+23+7+1, 51+32+30+23+8+1, 51+32+30+23+8+2+1, 51+32+30+23+8+3+1, 51+32+30+ 23+8+4+1, 51+32+30+23+8+4+2+1, 51+32+30+23+8+4+ 3+1, 51+32+30+23+8+5+1, 51+32+30+23+8+6+1, 51+32+ 30+23+8+7+1, 51+32+31+23+1, 51+32+31+23+2+1, 51+32+31+23+3+1, 51+32+31+23+4+1, 51+32+31+23+4+ 2+1, 51+32+31+23+4+3+1, 51+32+31+23+5+1, 51+32+ 31+23+6+1, 51+32+31+23+7+1, 51+32+31+23+8+1, 51+32+31+23+8+2+1, 51+32+31+23+8+3+1, 51+32+31+ 23+8+4+1, 51+32+31+23+8+4+2+1, 51+32+31+23+8+4+ 3+1, 51+32+31+23+8+5+1, 51+32+31+23+8+6+1, 51+32+ 31+23+8+7+1, 51+33+1, 51+33+2+1, 51+33+3+1, 51+33+ 4+1, 51+33+4+2+1, 51+33+4+3+1, 51+33+5+1, 51+33+6+ 1, 51+33+7+1, 51+33+8+1, 51+33+8+2+1, 51+33+8+3+1, 51+33+8+4+1, 51+33+8+4+2+1, 51+33+8+4+3+1, 51+33+ 8+5+1, 51+33+8+6+1, 51+33+8+7+1, 51+34+1, 51+34+2+ 1, 51+34+3+1, 51+34+4+1, 51+34+4+2+1, 51+34+4+3+1, 51+34+5+1, 51+34+6+1, 51+34+7+1, 51+34+8+1, 51+34+ 8+2+1, 51+34+8+3+1, 51+34+8+4+1, 51+34+8+4+2+1, 51+34+8+4+3+1, 51+34+8+5+1, 51+34+8+6+1, 51+34+8+ 7+1, 51+35+1, 51+35+2+1, 51+35+3+1, 51+35+4+1, 51+35+4+2+1, 51+35+4+3+1, 51+35+5+1, 51+35+6+1, 51+35+7+1, 51+35+8+1, 51+35+8+2+1, 51+35+8+3+1, 51+35+8+4+1, 51+35+8+4+2+1, 51+35+8+4+3+1, 51+35+ 8+5+1, 51+35+8+6+1, 51+35+8+7+1, 51+36+35+1, 51+36+35+2+1, 51+36+35+3+1, 51+36+35+4+1, 51+36+ 35+4+2+1, 51+36+35+4+3+1, 51+36+35+5+1, 51+36+35+ 6+1, 51+36+35+7+1, 51+36+35+8+1, 51+36+35+8+2+1, 51+36+35+8+3+1, 51+36+35+8+4+1, 51+36+35+8+4+2+1, 51+36+35+8+4+3+1, 51+36+35+8+5+1, 51+36+35+8+6+1, 51+36+35+8+7+1, 51+37+35+1, 51+37+35+2+1, 51+37+ 35+3+1, 51+37+35+4+1, 51+37+35+4+2+1, 51+37+35+4+ 3+1, 51+37+35+5+1, 51+37+35+6+1, 51+37+35+7+1, 51+37+35+8+1, 51+37+35+8+2+1, 51+37+35+8+3+1, 51+37+35+8+4+1, 51+37+35+8+4+2+1, 51+37+35+8+4+ 3+1, 51+37+35+8+5+1, 51+37+35+8+6+1, 51+37+35+8+ 7+1, 51+38+1, 51+39+38+1, 51+40+38+1, 51+40+39+38+ 1, 51+41, 51+42+38+1, 51+42+39+38+1, 51+42+40+38+1, 51+42+40+39+38+1, 51+42+41, 51+43+1, 51+44+43+1, 51+45+43+1, 51+46+43+1, 51+46+44+43+1 and 51+46+ 45+43+1.

In the list above, the numbers refer to the embodiments according to their numbering provided hereinabove whereas "+" indicates the dependency from another embodiment. The different individualised embodiments are separated by commas. In other words, "4+3+1" for example refers to embodiment 4) depending on embodiment 3), depending on embodiment 1), i.e. embodiment "4+3+1" corresponds to embodiment 1) further limited by the features of embodiments 3) and 4). Likewise, "11+9+8+1" refers to embodiment 11) depending mutatis mutandis on embodiments 9) and 8), depending on embodiment 1), i.e. embodiment "11+9+8+1" corresponds to embodiment 1) further limited by the features of embodiment 11), further limited by the features of embodiments 8) and 9).

The compounds of formula I can be manufactured in accordance with the present invention using the procedures described hereafter.
Preparation of the Compounds of Formula I
Abbreviations:
The following abbreviations are used throughout the specification and the examples:
Ac acetyl
AcOH acetic acid
Alloc allyloxycarbonyl
aq. aqueous
Boc tert-butoxycarbonyl
Bs 4-bromobenzenesulfonyl (brosylate)
Cbz benzyloxycarbonyl
CC column chromatography over silica gel
CDI 1,1'-carbonyldiimidazole
Cipro ciprofloxacin
DAD diode array detection
DCE 1,2-dichloroethane
DCM dichloromethane
DIPEA N,N-diisopropylethylamine
DMAP 4-dimethylaminopyridine
DMF N,N-dimethylformamide
DMSO dimethylsulfoxide
EA ethyl acetate
EDC N-(3-dimethylaminopropyl)-N'-ethylcarbodiimide hydrochloride
ELSD evaporative light scattering detector
ESI electron spray ionisation
eq. equivalent
Et ethyl
EtOH ethanol
Hept heptane
Hex hexane
HOBT 1-hydroxybenzotriazole
HPLC high pressure liquid chromatography
HV high vacuum conditions
LC liquid chromatography
Me methyl
MeCN acetonitrile
MeOH methanol
MS mass spectroscopy
Ms methanesulfonyl (mesyl)
Nf nonafluorobutanesulfonyl
Ns 4-nitrobenzenesulfonyl (nosylate)
org. organic
Pd/C palladium on carbon
Pd(OH)$_2$/C palladium dihydroxide on carbon
Ph phenyl
Pyr pyridine
rt room temperature
sat. saturated
TBAF tetra-n-butylammonium fluoride
TBDMS tert-butyldimethylsilyl
TBDPS tert-butyldiphenylsilyl
TBME tert-butyl methyl ether
tBu tert-butyl
TEA triethylamine
Tf trifluoromethanesulfonyl (triflyl)
TFA trifluoroacetic acid
THF tetrahydrofuran
TLC thin layer chromatography
$t_R$ retention time
Ts para-toluenesulfonyl
XantPhos 4,5-bis(diphenylphosphino)-9,9-dimethylxanthene General Reaction Techniques:
General Reaction Technique 1 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. $NaBH_4$, $NaBH_3CN$, or $NaBH(OAc)_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (Sato et al., *Tetrahedron* (2004), 60, 7899-7906).

General Reaction Technique 2 (Alkylation of an Amine with a Mesylate or an Iodide):

The amine derivative is reacted with the required iodide derivative or alcohol derivative activated as a sulfonate (OMs, ONf, ONs, OBs, OTf, OTs) in the presence of an inorganic base such as $K_2CO_3$ or an org. base such as TEA or DIPEA in a solvent such as THF, DMF or DMSO between 0° C. and +80° C. Further details can be found in *Comprehensive Organic Transformations. A guide to Functional Group Preparations*; $2^{nd}$ Edition, R. C. Larock, Wiley-VC; New York, Chichester, Weinheim, Brisbane, Singapore, Toronto, (1999) Section Amines, p. 779.

General Reaction Technique 3 (Alcohol Oxidation):

A primary allylic or benzylic alcohol dissolved in an organic solvent such as DCM or THF is oxidized into the corresponding aldehyde with $MnO_2$. Further methods can be found in *Comprehensive Organic Transformations. A guide to Functional Group Preparations*; $2^{nd}$ Edition, R. C. Larock, Wiley-VC; New York, Chichester, Weinheim, Brisbane, Singapore, Toronto, 1999; Section aldehydes and ketones, p. 1234-1236.

General Reaction Technique 4 (Alcohol Activation):

The alcohol is reacted with MSCl, TfCl, BsCl, NfCl, NsCl or TsCl in the presence of a base such as TEA in a dry aprotic solvent such as Pyr, THF or DCM between −30° C. and +50° C. In the case of the triflate or mesylate, $Tf_2O$ or $Ms_2O$ can also be used.

General Reaction Technique 5 (Formation of Iodo, Chloro or Bromo Derivatives):

The sulfonates obtained using general reaction technique 4 can be reacted with a sodium halogenide such as NaI or NaBr in MeCN or DMF between 40° C. and 120° C. delivering the corresponding iodide derivatives. Alternatively the corresponding bromides or chlorides can also be obtained by reaction of the corresponding alcohol derivatives with $PBr_3$ or $PCl_3$ respectively.

General Reaction Technique 6 (Removal of Amino Protecting Groups):

The Cbz protecting groups are removed by hydrogenolysis over a noble metal catalyst (e.g. Pd/C or $Pd(OH)_2/C$). The Boc group is removed under acidic conditions such as HCl in an org. solvent such as MeOH or dioxane, or TFA neat or diluted in a solvent such DCM. The Alloc group is removed in the presence of tetrakis(triphenylphosphine) palladium(0) in presence of an allyl cation scavenger such as morpholine, dimedone or tributyltin hydride between 0° C. and 50° C. in a solvent such as THF. The 4-methoxybenzyl group is removed using TFA neat or diluted in a solvent such DCM. Further general methods to remove amine protecting groups have been described in *Protecting Groups in Organic Synthesis*, $3^{rd}$ Ed (1999), 494-653; T. W. Greene, P. G. M. Wuts; (Publisher: John Wiley and Sons, Inc., New York, N.Y.).

General Reaction Technique 7 (Removal of Hydroxy Protecting Groups):

The silyl ether groups are removed either using fluoride anion sources such as TBAF in THF between 0° C. and +40° C. or HF in MeCN between 0° C. and +40° C. or using acidic conditions such as AcOH in THF/MeOH or HCl in MeOH. Further methods to remove the TBDMS and TBDPS groups are given in T. W. Greene, P. G. M. Wuts, *Protecting Groups in Organic Synthesis*, $3^{rd}$ Ed (1999), 133-139 and 142-143 respectively (Publisher: John Wiley and Sons, Inc., New York, N.Y.). The benzyl protecting group can be removed by catalytic hydrogenolysis over a noble metal catalyst such as Pd/C in a solvent such as MeOH or THF. Further general methods to remove alcohol protecting groups are described in T. W. Greene, P. G. M. Wuts, *Protecting Groups in Organic Synthesis*, $3^{rd}$ Ed (1999), 23-147 (Publisher: John Wiley and Sons, Inc., New York, N.Y.).

General Preparation Methods:
Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) and b) hereafter describe general methods for preparing compounds of formula I. If not indicated otherwise, the generic groups U and W are as defined for formula I. General synthetic methods used repeatedly throughout the text below are referenced to and described in the above section entitled "General reaction techniques". In some instances certain generic groups might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by:
a) reacting a compound of formula II

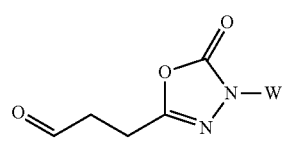

II wherein W has the same meaning as in formula I, with a compound of formula III

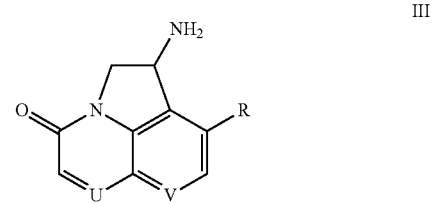

III wherein U, V and R have the same meanings as in formula I, using general reaction technique 1; or b) reacting a compound of formula III as defined in section a) with a compound of formula IV

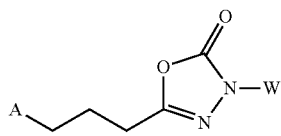

wherein W has the same meaning as in formula I and A represents a halogen such as iodine or the group $OSO_2R^A$ wherein $R^A$ represents alkyl, trifluoromethyl or tolyl, using general reaction technique 2.

The compounds of formula I thus obtained may, if desired, be converted into their salts, and notably into their pharmaceutically acceptable salts using standard methods.

Preparation of the Synthesis Intermediates:

Compounds of Formula II and IV:

The compounds of formulae II and IV can be prepared as summarised in Scheme 1 hereafter.

peptide coupling reagent such as EDC, followed by removal of the Boc protecting group using general reaction technique 6, affording the derivatives of formula I-2. The compounds of formula I-3 can be obtained by reacting the intermediates of formula I-2 with CDI. The compounds of formula I-3 can be further reacted with the derivatives of formula I-4 in the presence of (trans)-N,N'-di methyl-1,2-cyclohexanediamine and CuI, followed by the simultaneous removal of the protecting groups $PG^1$ and $R^{2A}$ with a mixture of TFA and trifluoromethanesulfonic acid, affording the derivatives of formula I-5. Alternatively the derivatives of formula I-1 can be reacted with the hydrazides derivatives of formula I-6 in presence of a peptide coupling reagent such as EDC to afford the derivatives of formula I-7 which are further cyclized by treatment with CDI, followed by the removal of the protecting group $PG^1$ with TFA or using general reaction technique 7, affording the derivatives of formula I-5 wherein W is different from the group $W^2$ as defined in formula I and $PG^1$ represents TBDMS or TBDPS. The resulting alcohol derivatives of formula I-5 can be oxydized into the aldehydes of formula II using general reaction technique 3 or transformed into the derivatives of formula IV wherein A is I or Br by reaction with a compound of formula $ClSO_2R^A$ wherein $R^A$ represents alkyl, trifluoromethyl or tolyl using Scheme 1

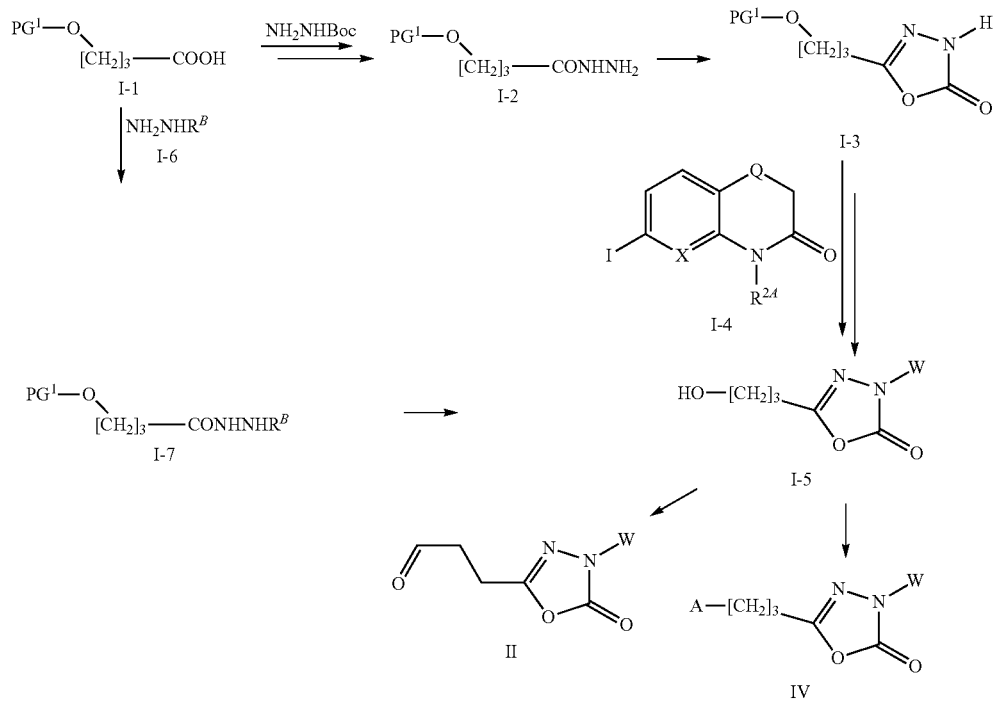

In Scheme 1, A represents a halogen such as iodine or the group $OSO_2R^A$ wherein $R^A$ represents alkyl, trifluoromethyl or tolyl, X, W and Q have the same meanings as in formula I, $PG^1$ represents an hydroxy protecting group such as benzyl, TBDMS or TBDPS, $R^B$ represents either a phenyl group substituted in para position with $(C_1-C_3)$alkyl, $(C_1-C_3)$alkoxy or $(C_1-C_3)$thioalkoxy and optionally in meta position with halogen, or the group of formula $W^2$ and $R^{2A}$ represents 4-methoxybenzyl.

The carboxylic acids of formula I-1 can be reacted (Scheme 1) with tert-butyl carbazate in the presence of a general reaction technique 4 followed by reaction of the resulting intermediate sulfonates with NaI or NaBr using general reaction technique 5.

Compounds of Formula III:

The compounds of formula III can be prepared as described in WO 2010/041194.

Intermediates Used in the Preparation of the Compounds of Formula II, III and IV:

The compounds of formula I-1 are either commercially available or can be prepared according to FR 2727412.

The compounds of formula I-4 can be prepared as summarised in Scheme 2 hereafter.

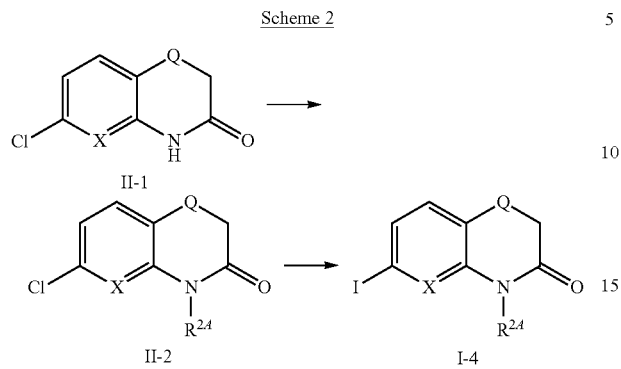

Scheme 2

In Scheme 2, Q and X have the same meanings as in formula I and $R^{2A}$ represents 4-methoxybenzyl.

The derivatives of formula II-1 (either commercially available or prepared according to WO 2012/041194, WO 01/30782 or Ramesh et al, *Tetrahedron* (2011), 67, 1187-1192) can be reacted with 4-methoxybenzyl chloride in the presence of NaH, affording the intermediates of formula II-2. The latter can be further transformed into the derivatives of formula I-4 by reaction with NaI in the presence of (trans)-N,N'-dimethyl-1,2-cyclohexanediamine and CuI The compounds of formula I-6 wherein $R^B$ represents either a phenyl group substituted in para position with $(C_1-C_3)$alkyl, $(C_1-C_3)$alkoxy or $(C_1-C_3)$thioalkoxy and optionally substituted in meta position with a fluorine, or a group of formula $W^2$ are obtained in analogy to WO 2008/054600 by diazotation of the commercially available aniline with $NaNO_2$ followed by reduction with tin chloride.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 $F_{254}$. Elution is performed with EA, Hept, DCM, MeOH or mixtures thereof. Detection was done with UV or with a solution of $KMnO_4$ (3 g), $K_2CO_3$ (20 g), 5% NaOH (3 mL) and $H_2O$ (300 mL) with subsequent heating.

CCs were performed using Brunschwig 60A silica gel (0.032-0.63 mm), elution being carried out with EA, Hept, DCM, MeOH or mixtures thereof. When the compounds contained an acid function, 1% of AcOH was added to the eluent(s). $NH_4OH$ as used for CC is 25% aq.

The compounds were characterized by $^1$H-NMR (300 MHz, Varian Oxford; 400 MHz, Bruker Avance 400 or 500 MHz, Bruker Avance 500 Cryoprobe). Chemical shifts δ are given in ppm relative to the solvent used; multiplicities: s=singlet, d=doublet, t=triplet, q=quartet, p=pentet, hex=hexet, hep=heptet, m=multiplet, br.=broad; coupling constants J are given in Hz. Alternatively compounds were characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 $F_{254}$); or by melting point.

The analytical LC-MS data have been obtained using the following respective conditions:
MS1 data:
  Column: Zorbax SB-Aq, 3.5 μm, 4.6×50 mm;
  Injection volume: 1 μL;
  Column oven temperature: 40° C.;
  Pump: Dionex HPG-320016;
  Makeup pump: Dionex ISO-31005D;
  DAD: Dionex DAD-3000016;
  MS: Thermo MSQ Plus;
  ELSD: Sedere Sedex 85;
  Detection: UV 210 nm, ELSD and MS;
  MS ionization mode: ESI+;
  Eluents: A: $H_2O$+0.04% TFA; and B: MeCN;
  Eluent flow rate: 4.5 mL/min;
  Gradient: 5% B to 95% B (0.0 min-1.0 min), 95% B (1.0 min-1.45 min)
MS2 data:
  Column: Waters Atlantis T3, 5 μm, 4.6×30 mm;
  otherwise same parameters as for obtaining MS1 data.
MS3 data:
  Column: Zorbax SB-Aq, 3.5 μm, 4.6×50 mm;
  Injection volume: 1 μL;
  Column oven temperature: 40° C.;
  Pump: Agilent G4220A;
  Makeup pump: Dionex HPG-32005D;
  DAD: Agilent G4212A;
  MS: Thermo MSQ Plus;
  ELSD: Sedere Sedex 90;
  Detection: UV 210 nm, ELSD and MS;
  MS ionization mode: ESI+;
  Eluents: A: $H_2O$+0.04% TFA; and B: MeCN;
  Flow rate: 4.5 mL/min;
  Gradient: 5% B to 95% B (0.00 min-1.07 min), 95% B (1.07 min-1.57 min).

The number of decimals given for the corresponding [M+H$^+$] peak(s) of each tested compound depends upon the accuracy of the LC-MS device actually used.

The prep-HPLC purifications were performed on a Gilson HPLC system, equipped with a Gilson 215 autosampler, Gilson 333/334 pumps, Dionex MSQ Plus detector system, and a Dionex UVD340U (or Dionex DAD-3000) UV detector, using the following conditions:
Method 1:
  Column: Waters Atlantis T3 OBD, 10 μm, 30×75 mm;
  Flow rate: 75 mL/min;
  Eluents: A: $H_2O$+0.1% HCOOH; B: MeCN+0.1% HCOOH;
  Gradient: 80% A to 5% A (0.0 min-4.0 min), 5% A (4.0 min-6.0 min).
Method 2:
  Column: Waters Atlantis T3 OBD, 10 μm, 30×75 mm;
  Flow rate: 75 mL/min;
  Eluents: A: $H_2O$+0.1% HCOOH; B: MeCN+0.1% HCOOH;
  Gradient: 95% A to 50% A (0.0 min 3.0 min), 50% A to 5% A (3.0 min-4.0 min), 5% A (4.0 min-6.0 min).

Preparations

Preparation A:
5-(3-benzyloxy-propyl)-3H-[1,3,4]oxadiazol-2-one

A.i. Tert-butyl 2-(4-(benzyloxy)butanoyl)hydrazinecarboxylate

A solution of 4-(benzyloxy)butyric acid (15.5 g, commercial), tert-butyl carbazate (12.2 g) and EDC (23.92 g) in DCM (300 mL) was stirred under argon for 2 h. The reaction mixture was sequentially washed with a sat. NH$_4$Cl solution and brine, dried over MgSO$_4$ and concentrated under reduced pressure. The residue was purified by CC with Hept/EA (1:2 to 0:1), affording a colourless oil (22.8 g; 93% yield).

MS1 (ESI, m/z): 309.1 [M+H$^+$]; t$_R$=0.76 min.

A.ii. 4-benzyloxy-butyric acid hydrazide

A solution of intermediate A.i (22.5 g) in DCM (150 mL) was treated with TFA (112 mL) and further stirred at rt for 1 h. The reaction mixture was concentrated to dryness and taken up in DCM (150 mL), treated with a sat aq. NH$_4$OH solution. The aq. layer was extracted twice with DCM. The combined org. layers were washed with brine, dried over MgSO$_4$ and concentrated under reduced pressure, affording an off-white solid (13.0 g; 85% yield).

MS1 (ESI, m/z): 209.3 [M+H$^+$]; t$_R$=0.5 min.

A.iii. 5-(3-benzyloxy-propyl)-3H-[1,3,4]oxadiazol-2-one

A solution of intermediate A.ii (12.9 g) in DCE (280 mL) was treated with CDI (20.1 g) and the reaction mixture was heated to 80° C. for 1 h. The reaction mixture was concentrated under reduced pressure. The residue was purified by CC with Hept/EA (1:1), affording a colourless oil (10.6 g; 73% yield).

MS3 (ESI, m/z): 235.3 [M+H$^+$]; t$_R$=0.71 min.

Preparation B: 3-[5-oxo-4-(4-propyl-phenyl)-4,5-dihydro-[1,3,4]oxadiazol-2-yl]-propionaldehyde B.i. 5-(3-benzyloxy-propyl)-3-(4-propyl-phenyl)-3H-[1,3,4]oxadiazol-2-one A suspension of K$_2$CO$_3$ (982 mg), copper(I) iodide (136 mg) and (trans)-N,N'-dimethyl-1,2-cyclohexanediamine (0.112 mL) was purged with argon for 5 min. A solution of 1-iodo-4-(n-propyl)benzene (657 mg) and the compound of Preparation A (500 mg) in DMF (14 mL) was added and the mixture was stirred at 110° C. overnight. The mixture was allowed to reach rt and filtered over a glass-fibre filter. The solid was washed with EA and the filtrate was diluted with EA and washed with sat. aq. NH$_4$Cl. The aq. layer was extracted twice with EA. The combined org. layers were washed twice with water and brine, dried over MgSO$_4$ and concentrated under reduced pressure. The residue was purified by CC with Hept/EA (1:1), affording a brown solid (631 mg; 100% yield).

MS3 (ESI, m/z): 353.2 [M+H$^+$]; t$_R$=1.05 min.

B.ii. 5-(3-hydroxy-propyl)-3-(4-propyl-phenyl)-3H-[1,3,4]oxadiazol-2-one

A solution of intermediate B.i (600 mg) in DCM (90 mL) was treated with TFA (6.5 mL) and trifluoromethanesulfonic acid (1.5 mL) and further stirred at rt for 30 min. The reaction mixture was cooled to 0° C. and treated dropwise with a solution of TEA (20 mL) in MeOH (20 mL). The reaction mixture was diluted with water and DCM. The org. layer was separated and the aq. layer was extracted with DCM. The combined org. layers were sequentially washed with 0.1N HCl, water and brine, dried over MgSO$_4$ and concentrated under reduced pressure. The residue was purified by CC with Hept/EA (1:1), affording a brown oil (278 mg; 62% yield).

MS3 (ESI, m/z): 263.3 [M+H$^+$]; t$_R$=0.83 min.

B.iii. 3-[5-oxo-4-(4-propyl-phenyl)-4,5-dihydro-[1,3,4]oxadiazol-2-yl]-propionaldehyde A solution of intermediate B.ii (250 mg) and DIPEA (0.5 mL) in DCM (7 mL) was cooled to 10° C. and treated dropwise over 5 min with a solution of SO$_3$.Pyr complex (304 mg) in DMSO (1.4 mL). The reaction mixture was allowed to reach rt and further stirred at this temperature for 1 h. The reaction mixture was diluted with DCM and washed with 1M HCl, water and brine, dried over MgSO$_4$ and concentrated under reduced pressure. The residue was stirred in TBME and filtered, affording a brown oil (135 mg; 54% yield).

$^1$H NMR (CDCl$_3$) δ: 9.87 (s, 1H); 7.68 (d, J=8.7 Hz, 2H); 7.23 (m, 2H); 2.98 (m, 4H); 2.59 (m, 2H); 1.62 (m, 2H); 0.93 (t, J=7.3 Hz, 3H).

Preparation C: 3-[4-(4-isopropyl-phenyl)-5-oxo-4,5-dihydro-[1,3,4]oxadiazol-2-yl]-propionaldehyde C.i. 4-(tert-butyl-dimethyl-silanyloxy)-butyric acid N'-(4-isopropyl-phenyl)-hydrazide A solution of 4-[(tert-butyldimethylsilanyl)oxy]butyric acid (1.2 g) in DMF (20 mL) was treated at rt with DIPEA (2.4 mL), HOBT (891 mg) and EDC (1.32 g). The resulting solution was treated with 4-isopropylphenylhydrazine hydrochloride (1.03 g) and further stirred at rt overnight. The reaction mixture was diluted with a 10% aq. citric acid solution and EA. The aq. layer was extracted with EA and the combined org. layers were sequentially washed with a sat. NaHCO$_3$ solution and brine, dried over MgSO$_4$ and concentrated under reduced pressure. The residue was purified by CC with Hept/EA (4:1), affording an orange oil (1.07 g; 55% yield).

MS2 (ESI, m/z): 351.4 [M+H$^+$]; t$_R$=1.09 min.

C.ii. 5-(3-hydroxy-propyl)-3-(4-isopropyl-phenyl)-3H-[1,3,4]oxadiazol-2-one

A solution of intermediate C.i (35 mg) in THF (1 mL) was treated with triphosgene (15 mg) and the mixture was stirred at 50° C. for 1 h. The reaction mixture was allowed to reach rt and was quenched by the addition of water (5 mL). The reaction mixture was diluted with EA and the org. layer was separated. The aq. layer was extracted with EA. The combined org. layers were sequentially washed with water, a sat. NaHCO$_3$ solution and brine, dried over MgSO$_4$ and concentrated under reduced pressure. The residual white solid (20 mg, 76% yield) was directly used in the next step.

MS2 (ESI, m/z): 263.4 [M+H$^+$]; t$_R$=0.82 min.

C.iii. 3-[4-(4-isopropyl-phenyl)-5-oxo-4,5-dihydro-[1,3,4]oxadiazol-2-yl]-propionaldehyde Starting from intermediate C.ii (20 mg) and proceeding in analogy to Preparation B, step B.iii, the title compound was obtained as a brown oil (20 mg, 100% yield).

MS2 (ESI, m/z): 259.4 [M+H$^+$]; t$_R$=0.89 min.

Preparation D: 3-[4-(4-ethylsulfanyl-phenyl)-5-oxo-4,5-dihydro-[1,3,4]oxadiazol-2-yl]-propionaldehyde

D.i. 5-(3-benzyloxy-propyl)-3-(4-ethylsulfanyl-phenyl)-3H-[1,3,4]oxadiazol-2-one Starting from the compound of Preparation A (500 mg) and 1-bromo-4-(ethylthio)benzene (386 mg; commercial) and proceeding in analogy to Preparation B, step B.i, the title compound was obtained as a brown oil (499 mg, 76% yield).

MS1 (ESI, m/z): 371.3 [M+H$^+$]; $t_R$=1.03 min.

D.ii. 3-(4-ethylsulfanyl-phenyl)-5-(3-hydroxy-propyl)-3H-[1,3,4]oxadiazol-2-one Starting from intermediate D.i (460 mg) and proceeding in analogy to Preparation B, step B.ii, the title compound was obtained as an orange oil (114 mg, 33% yield).

MS3 (ESI, m/z): 281.3 [M+H+]; $t_R$=0.81 min.

D.iii. 3-[4-(4-ethylsulfanyl-phenyl)-5-oxo-4,5-dihydro-[1,3,4]oxadiazol-2-yl]-propionaldehyde Starting from intermediate D.ii (100 mg) and proceeding in analogy to Preparation B, step B.iii, the title compound was obtained as a yellow oil (100 mg, 100% yield).

$^1$H NMR (CDCl$_3$) δ: 9.87 (s, 1H); 7.73 (m, 2H), 7.38 (m, 2H), 2.95 (m, 6H), 1.31 (t, J=7.3 Hz, 3H).

Preparation E: 3-[5-oxo-4-(3-oxo-3,4-dihydro-2H-pyrido[3,2-b][1,4]oxazin-6-yl)-4,5-dihydro-[1,3,4]oxadiazol-2-yl]-propionaldehyde

E.i. 6-[5-(3-benzyloxy-propyl)-2-oxo-[1,3,4]oxadiazol-3-yl]-4-(4-methoxy-benzyl)-4H-pyrido[3,2-b][1,4]oxazin-3-one Starting from the compound of Preparation A (2.00 g) and 6-bromo-4-[(4-methoxyphenyl)methyl]-2H-pyrido[3,2-b]-1,4-oxazin-3(4H)-one (2.48 g; prepared according to WO 2009/104159), and proceeding in analogy to Preparation B, step B.i, the title compound was obtained as a yellow oil (2.81 g; 79% yield).

MS1 (ESI, m/z): 503.3 [M+H$^+$]; $t_R$=0.99 min.

E.ii. 6-(5-(3-hydroxypropyl)-2-oxo-1,3,4-oxadiazol-3(2H)-yl)-2H-pyrido[3,2-b][1,4]oxazin-3(4H)-one Starting from intermediate E.i (1.60 g) and proceeding in analogy to Preparation B, step B.ii, the title compound was obtained as a yellow solid (260 mg; 28% yield).

MS3 (ESI, m/z): 293.3 [M+H$^+$]; $t_R$=0.55 min.

E.iii. 3-[5-oxo-4-(3-oxo-3,4-dihydro-2H-pyrido[3,2-b][1,4]oxazin-6-yl)-4,5-dihydro-[1,3,4]oxadiazol-2-yl]-propionaldehyde Starting from intermediate E.ii (50 mg) and proceeding in analogy to Preparation B, step B.iii, the title compound was obtained as a yellow solid (41 mg, 83% yield).

MS3 (ESI, m/z): 291.2 [M+H$^+$]; $t_R$=0.56 min.

Preparation F: 3-[5-oxo-4-(3-oxo-3,4-dihydro-2H-benzo[1,4]oxazin-6-yl)-4,5-dihydro-[1,3,4]oxadiazol-2-yl]-propionaldehyde

F.i. 6-bromo-4-(4-methoxy-benzyl)-4H-benzo[1,4]oxazin-3-one

A suspension of 6-bromo-2H-1,4-benzoxazin-3(4H)-one (1.70 g; commercial), Cs$_2$CO$_3$ (2.9 g) and 4-methoxybenzyl chloride (1.12 mL) in DMF (30 mL) was stirred at rt for 2 h. The reaction mixture was partitioned between EA and water. The aq. layer was extracted with EA and the combined org. layers were washed with water and brine, dried over MgSO$_4$ and concentrated under reduced pressure. The residue was triturated with TBME/EA, filtered and dried under HV, affording an off-white solid (2.30 g; 89% yield).

MS3 (ESI, m/z): 348.1 [M+H$^+$]; $t_R$=0.93 min.

F.ii. 6-[5-(3-benzyloxy-propyl)-2-oxo-[1,3,4]oxadiazol-3-yl]-4-(4-methoxy-benzyl)-4H-benzo[1,4]oxazin-3-one Starting from the compound of Preparation A (50 mg) and intermediate F.i (619 mg), and proceeding in analogy to Preparation B, step B.i, the title compound was obtained as a yellow oil (350 mg; 39% yield).

MS3 (ESI, m/z): 502.2 [M+H$^+$]; $t_R$=1.00 min.

F.iii. 6-(5-(3-hydroxypropyl)-2-oxo-1,3,4-oxadiazol-3(2H)-yl)-2H-benzo[b][1,4]oxazin-3(4H)-one Starting from intermediate F.ii (330 mg) and proceeding in analogy to Preparation B, step B.ii, the title compound was obtained as a brown solid (78 mg, 44% yield).

MS3 (ESI, m/z): 333.2 [M+H$^+$] (MeCN-adduct); $t_R$=0.60 min.

F.iv. 3-[5-oxo-4-(3-oxo-3,4-dihydro-2H-benzo[1,4]oxazin-6-yl)-4,5-dihydro-[1,3,4]oxadiazol-2-yl]-propionaldehyde Starting from intermediate F.iii (130 mg) and proceeding in analogy to Preparation B, step B.iii, the title compound was obtained as a yellow oil (191 mg; quantitative yield).

MS3 (ESI, m/z): 331.2 [M+H$^+$] (MeCN-adduct); $t_R$=0.61 min.

Preparation G: 3-[5-oxo-4-(3-oxo-3,4-dihydro-2H-pyrido[3,2-b][1,4]thiazin-6-yl)-4,5-dihydro-[1,3,4]oxadiazol-2-yl]-propionaldehyde

G.i. 6-chloro-4-(4-methoxy-benzyl)-4H-pyrido[3,2-b][1,4]thiazin-3-one

Starting from 6-chloro-2H-pyrido[3,2-b]-1,4-thiazin-3(4H)-one (2.00 g; prepared according to WO 2010/041194) and 4-methoxy-benzylchloride (1.72 g), and proceeding in analogy to Preparation F, step F.i, the title compound was obtained as an off-white solid (2.84 g; 89% yield).

MS3 (ESI, m/z): 321.1 [M+H$^+$]; $t_R$=0.93 min.

G.ii. 6-iodo-4-(4-methoxy-benzyl)-4H-pyrido[3,2-b][1,4]thiazin-3-one

A solution of intermediate G.i (1.60 g) in dioxane (8 mL) was treated with (trans)-N,N'-dimethyl-1,2-cyclohexanediamine (0.315 mL), NaI (1.49 g) and copper(I) iodide (190 mg). The reaction mixture was heated overnight at 80° C. for 3 days, allowed to reach rt and filtered over Celite. The filter cake was washed with EA (2×20 mL) and the filtrate was washed with water (150 mL) and extracted with EA (150 mL). The aq. layer was extracted with EA (2×150 mL). The combined org. layers were washed with brine (100 mL), dried over MgSO$_4$ and concentrated under reduced pressure. The residue was purified by CC (Hept/EA 1:1), affording a yellow solid (1.28 g; 62% yield).

MS3 (ESI, m/z): 413.1 [M+H$^+$]; $t_R$=0.96 min.

G.iii. 6-[5-(3-benzyloxy-propyl)-2-oxo-[1,3,4]oxadiazol-3-yl]-4-(4-methoxy-benzyl)-4H-pyrido[3,2-b][1,4]thiazin-3-one Starting from the compound of Preparation A (773 mg) and intermediate G.ii (1260 mg), and proceeding in analogy to Preparation B, step B.i, the title compound was obtained as a brown oil (580 mg; 41% yield).

MS3 (ESI, m/z): 519.2 [M+H$^+$]; $t_R$=1.02 min.

G.iv. 5-(3-hydroxypropyl)-3-(3-oxo-3,4-dihydro-2H-pyrido[3,2-b][1,4]thiazin-6-yl)-1,3,4-oxadiazol-2(3H)-one Starting from intermediate G.iii (560 mg) and proceeding in analogy to Preparation B, step B.ii, the title compound was obtained as an orange foam (349 mg; 100% yield).

MS3 (ESI, m/z): 309.2 [M+H$^+$]; $t_R$=0.60 min.

G.v. 3-[5-oxo-4-(3-oxo-3,4-dihydro-2H-pyrido[3,2-b][1,4]thiazin-6-yl)-4,5-dihydro-[1,3,4]oxadiazol-2-yl]-propionaldehyde Starting from intermediate G.iv (376 mg) and proceeding in analogy to Preparation B, step B.iii, the title compound was obtained (347 mg, 93% yield).

MS3 (ESI, m/z): 307.13 [M+H$^+$]; $t_R$=0.60 min.

Preparation H: 3-[5-oxo-4-(3-oxo-3,4-dihydro-2H-benzo[1,4]thiazin-6-yl)-4,5-dihydro-[1,3,4]oxadiazol-2-yl]-propionaldehyde H.i. 6-[5-(3-benzyloxy-propyl)-2-oxo-[1,3,4]oxadiazol-3-yl]-4H-benzo[1,4]thiazin-3-one Starting from the compound of Preparation A (396 mg) and 6-iodo-2H-1,4-benzothiazin-3(4H)-one (1260 mg; prepared according to Mackie et al, *J. Chem. Soc.* (1952), 787-790), and proceeding in analogy to Preparation B, step B.i, the title compound was obtained as an orange solid (115 mg, 21% yield).

MS3 (ESI, m/z): 439.3 [M+H$^+$] (MeCN-adduct); $t_R$=0.90 min.

H.ii. 5-(3-hydroxypropyl)-3-(3-oxo-3,4-dihydro-2H-benzo[b][1,4]thiazin-6-yl)-1,3,4-oxadiazol-2(3H)-on Starting from intermediate H.i (70 mg) and proceeding in analogy to Preparation B, step B.ii, the title compound was obtained as a beige solid (31 mg, 57% yield).

MS3 (ESI, m/z): 308.1 [M+H$^+$]; $t_R$=0.65 min.

H.iii. 3-[5-oxo-4-(3-oxo-3,4-dihydro-2H-benzo[1,4]thiazin-6-yl)-4,5-dihydro-[1,3,4]oxadiazol-2-yl]-propionaldehyde Starting from intermediate H.ii (25 mg) and proceeding in analogy to Preparation B, step B.iii, the title compound was obtained as a beige solid (30 mg).

MS3 (ESI, m/z): 347.2 [M+H$^+$] (MeCN-adduct); $t_R$=0.65 min.

Preparation I: 3-[4-(2,3-dihydro-benzo[1,4]dioxin-6-yl)-5-oxo-4,5-dihydro-[1,3,4]oxadiazol-2-yl]-propionaldehyde I.i. 5-(3-benzyloxy-propyl)-3-(2,3-dihydro-benzo[1,4]dioxin-6-yl)-3H-[1,3,4]oxadiazol-2-one Starting from the compound of Preparation A (700 mg) and 6-iodo-2,3-dihydro-1,4-benzodioxine (807 mg; commercial), and proceeding in analogy to Preparation B, step B.i, the title compound was obtained as a yellow solid (397 mg, 36% yield).

MS3 (ESI, m/z): 369.4 [M+H$^+$]; $t_R$=0.95 min.

I.ii. 3-(2,3-dihydrobenzo[b][1,4]dioxin-6-yl)-5-(3-hydroxypropyl)-1,3,4-oxadiazol-2(3H)-one Starting from intermediate I.i (370 mg) and proceeding in analogy to Preparation B, step B.ii, the title compound was obtained as a yellow oil (115 mg, 41% yield).

MS3 (ESI, m/z): 320.3 [M+MeCN+H$^+$]; $t_R$=0.69 min.

I.iii. 3-[4-(2,3-dihydro-benzo[1,4]dioxin-6-yl)-5-oxo-4,5-dihydro-[1,3,4]oxadiazol-2-yl]-propionaldehyde Starting from intermediate I.ii (100 mg) and proceeding in analogy to Preparation B, step B.iii, the title compound was obtained as a light yellow oil (72 mg; 73% yield).

MS3 (ESI, m/z): 318.2 [M+MeCN+H$^+$]; $t_R$=0.72 min.

Preparation J: 3-[4-(4-ethoxy-phenyl)-5-oxo-4,5-dihydro-[1,3,4]oxadiazol-2-yl]-propionaldehyde J.i 5-(3-benzyloxy-propyl)-3-(4-ethoxy-phenyl)-3H-[1,3,4]oxadiazol-2-one Starting from the compound of Preparation A (700 mg) and 4-iodophenetole (741 mg; commercial), and proceeding in analogy to Preparation B, step B.i, the title compound was obtained as a yellow oil (632 mg; 60% yield).

MS3 (ESI, m/z): 355.4 [M+H$^+$]; $t_R$=0.98 min.

J.ii 3-(4-ethoxy-phenyl)-5-(3-hydroxy-propyl)-3H-[1,3,4]oxadiazol-2-one

Starting from intermediate J.i (600 mg) and proceeding in analogy to Preparation B, step B.ii, the title compound was obtained as an orange oil (276 mg, 35% yield).

MS3 (ESI, m/z): 306.3 [M+MeCN+H$^+$]; $t_R$=0.74 min.

J.iii. 3-[4-(4-ethoxy-phenyl)-5-oxo-4,5-dihydro-[1,3,4]oxadiazol-2-yl]-propionaldehyde Starting from intermediate J.ii (250 mg) and proceeding in analogy to Preparation B, step B.iii, the title compound was obtained as a yellow solid (166 mg; 67% yield).

MS3 (ESI, m/z): 304.3 [M+MeCN+H$^+$]; $t_R$=0.78 min.

Preparation K: (S)-1-amino-9-methoxy-1H-pyrrolo[3,2,1-ij]quinolin-4(2H)-one

K.i. (S)-tert-butyl (9-methoxy-4-oxo-2,4-dihydro-1H-pyrrolo[3,2,1-ij]quinolin-1-yl)carbamate A solution of (S)-tert-butyl (9-fluoro-4-oxo-2,4-dihydro-1H-pyrrolo[3,2,1-ij]quinolin-1-yl)carbamate (150 mg; prepared in analogy to WO 2010/041194) in THF/MeOH (1:1; 4 mL) was reacted with LiOH (hydrate; 62 mg) at 60° C. overnight. The reaction mixture was evaporated under reduced pressure. The residue was dissolved in EA, sequentially washed with water and brine, dried over MgSO$_4$ and concentrated under reduced pressure, affording a beige solid (142 mg; 91% yield).
MS1 (ESI, m/z): 316.94 [M+H$^+$]; $t_R$=0.75 min.

K.ii. (S)-1-amino-9-methoxy-1H-pyrrolo[3,2,1-ij]quinolin-4(2H)-one

A solution of intermediate K.i (120 mg) in DCM (3 mL) was treated with TFA (0.5 mL) and further stirred at rt for 1 h. The solution was evaporated under reduced pressure and the residue was dissolved in DCM and washed with a conc. aq. NH$_4$OH solution. The aq. layer was backwashed twice with DCM. The combined org. layers were dried over MgSO$_4$, filtered and concentrated under reduced pressure, affording an off-white solid (63 mg; 58% yield).
MS1 (ESI, m/z): 217.12 [M+H$^+$]; $t_R$=0.41 min.

Preparation L: (S)-1-amino-9-methyl-1H-pyrrolo[3,2,1-ij]quinolin-4(2H)-one

L.i. (S)-tert-butyl (9-(benzyloxy)-4-oxo-2,4-dihydro-1H-pyrrolo[3,2,1-ij]quinolin-1-yl)carbamate A suspension of NaH (60% suspension in oil; 591 mg) in THF (20 mL) was treated with benzyl alcohol (1.7 mL) and further stirred at rt for 15 min. The resulting suspension was treated with (S)-tert-butyl (9-fluoro-4-oxo-2,4-dihydro-1H-pyrrolo[3,2,1-ij]quinolin-1-yl)carbamate (1000 mg; prepared in analogy to WO 2010/041194) and further stirred at rt overnight. The reaction mixture was cooled to 0° C., treated with water and extracted with DCM/MeOH (9:1). The org. layer was sequentially washed with water and brine, dried over MgSO$_4$ and concentrated under reduced pressure. The oily material was purified by CC (DCM/MeOH 1:0 to 9:1), affording a colourless solid (1280 mg, 99% yield).
MS1 (ESI, m/z): 392.95 [M+H$^+$]; $t_R$=0.89 min.

L.ii. (S)-tert-butyl (9-hydroxy-4-oxo-2,4-dihydro-1H-pyrrolo[3,2,1-ij]quinolin-1-yl)carbamate A suspension of intermediate L.i (1100 mg) in MeOH (20 mL) was hydrogenated over Pd/C (10%; 309 mg) for 1 h. The catalyst was filtered off and the filtrate was evaporated under reduced pressure affording a colorless solid (748 mg, 88% yield).
MS1 (ESI, m/z): 302.94 [M+H$^+$]; $t_R$=0.72 min.

L.iii. (S)-1-((tert-butoxycarbonyl)amino)-4-oxo-2,4-dihydro-1H-pyrrolo[3,2,1-ij]quinolin-9-yl trifluoromethanesulfonate A suspension of intermediate L.ii (300 mg) in dry DCM (10 mL) was cooled to 0° C. and treated with 2,6-lutidine (159 mg). The reaction mixture was further stirred at this temperature for 15 min, cooled down to −78° C. and treated dropwise with trifluoromethanesulfonic anhydride (3 mL). The reaction mixture was further stirred at this temperature for 2 h, allowed to reach 0° C. and quenched with water. The reaction mixture was extracted with DCM/MeOH (9:1). The org. layer was sequentially washed with 1M HCl, water and brine, dried over MgSO$_4$ and concentrated under reduced pressure, affording a colourless solid (314 mg, 73% yield).
MS1 (ESI, m/z): 434.84 [M+H$^+$]; $t_R$=0.87 min.

L.iv. (S)-tert-butyl (9-methyl-4-oxo-2,4-dihydro-1H-pyrrolo[3,2,1-ij]quinolin-1-yl)carbamate A mixture of intermediate L.iii (265 mg), potassium methyltrifluoroborate (112 mg), CsCO$_3$ (608 mg) and [1,1'-bis(diphenylphosphino)ferrocene]dichloropalladium(II), complex (149 mg) were placed in a sealed flask and degassed with nitrogen. The mixture was treated with THF/H$_2$O (10:1) and heated at 60° C. for 4 days. The reaction mixture was quenched with water and extracted with DCM/MeOH (9:1). The combined org. layers were sequentially washed with water and brine, dried over MgSO$_4$ and concentrated under reduced pressure. The solid was purified by CC (DCM/MeOH 1:0 to 9:1), affording an off-white solid (167 mg, 91% yield).
MS1 (ESI, m/z): 301.00 [M+H$^+$]; $t_R$=0.77 min.

L.v. (S)-1-amino-9-methyl-1H-pyrrolo[3,2,1-ij]quinolin-4(2H)-one

A solution of intermediate L.iv (114 mg) in DCM (3 mL) was treated with TFA (0.75 mL) and further stirred at rt for 1 h. The solution was extracted with 1M HCl and washed with DCM. The aq. phase was treated with conc aq. NaOH to set the pH at 10, the aq. phase was extracted twice with DCM/MeOH (9:1). The combined org. layers were sequentially washed with water and brine, dried over MgSO$_4$ and concentrated under reduced pressure, affording a beige solid (72 mg, 95% yield).
MS1 (ESI, m/z): 201.14 [M+H$^+$]; $t_R$=0.41 min.

Preparation M: (S)-1-amino-4-oxo-1,2-dihydro-4H-pyrrolo[3,2,1-ij]quinoline-9-carbonitrile M.i. ((S)-9-cyano-4-oxo-1,2-dihydro-4H-pyrrolo[3,2,1-ij]quinolin-1-yl)-carbamic acid tert-butyl ester A mixture of intermediate L.iii (250 mg), zinc cyanide (69 mg), tris(dibenzylideneacetone)dipalladium(0) (158 mg) and 1,1'-bis(diphenylphosphino)ferrocene (191 mg) were placed in a sealed flask and degassed with nitrogen. The mixture was treated with DMF (5 mL) and heated overnight at 85° C. The reaction mixture was quenched with water and extracted twice with DCM/MeOH (9:1). The combined org. layers were sequentially washed with water and brine, dried over MgSO$_4$ and concentrated under reduced pressure. The solid was purified by CC (DCM/MeOH 1:0 to 9:1), affording a colourless solid (162 mg, 90% yield).
MS1 (ESI, m/z): 311.96 [M+H$^+$]; $t_R$=0.71 min.

M.ii. (S)-1-amino-4-oxo-1,2-dihydro-4H-pyrrolo[3,2,1-ij]quinoline-9-carbonitrile A solution of intermediate M.i (54 mg) in DCM (3 mL) was treated with TFA (0.5 mL) and further stirred at rt overnight. The solution was evaporated to dryness. The residue was dissolved in DCM and washed with a conc. aq. NH₄OH solution. The aq. layer was extracted twice with DCM. The combined org. layers were sequentially washed with water and brine, dried over MgSO₄ and concentrated under reduced pressure, affording an off-white solid (17 mg, 46% yield).

¹H NMR (500 MHz, DMSO) δ: 8.02 (d, J=9.5 Hz, 1H); 7.76 (d, J=7.9 Hz, 1H); 7.55 (d, J=8.1 Hz, 1H); 6.76 (d, J=9.5 Hz, 1H); 4.94 (dd, J=4.0, 8.3 Hz, 1H); 4.51 (dd, J=8.5, 12.6 Hz, 1H); 3.92 (dd, J=4.1, 12.6 Hz, 1H); 2.45 (m, 2H).

Examples of Compounds According to the Invention

Example 1

(S)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one A solution of (S)-1-amino-9-fluoro-1,2-dihydro-pyrrolo[3,2,1-ij]quinolin-4-one (31 mg; prepared according to WO 2010/041194) and the compound of Preparation B (40 mg) in DCM/MeOH (1:1, 1 mL) was treated with NaBH(OAc)₃ (130 mg) and stirred at rt for 2 h. The mixture was partitioned between sat. NaHCO₃ and DCM. The org. phase was separated, dried over MgSO₄ and concentrated under reduced pressure, affording a yellow oil (39 mg; 57% yield).
MS1 (ESI, m/z): 449.1 [M+H⁺]; $t_R$=0.72 min.

Example 2

(R)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one Starting from (R)-6-amino-7-fluoro-5,6-di hydro-pyrrolo[1,2,3-de]quinoxalin-3-one (32 mg; prepared according to WO 2010/041194) and the compound of Preparation B (40 mg), and proceeding in analogy to Example 1, the title compound was obtained as an orange oil (42 mg; 60% yield).
MS1 (ESI, m/z): 450.3 [M+H⁺]; $t_R$=0.72 min.

Example 3

(S)-9-fluoro-1-{3-[4-(4-isopropyl-phenyl)-5-oxo-4,5-dihydro-[1,3,4]oxadiazol-2-yl]-propylamino}-1,2-dihydro-pyrrolo[3,2,1-ij]quinolin-4-one Starting from (S)-1-amino-9-fluoro-1,2-dihydro-pyrrolo[3,2,1-ij]quinolin-4-one (15 mg; prepared according to WO 2010/041194) and the compound of Preparation B (19 mg), and proceeding in analogy to Example 1, the title compound was obtained, after purification by CC (DCM/MeOH 19:1+ 1% NH₄OH), as a colourless solid (7 mg; 21% yield).
MS2 (ESI, m/z): 449.4 [M+H⁺]; $t_R$=0.66 min.

Example 4

(S)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one Starting from (S)-1-amino-9-fluoro-1,2-di hydro-pyrrolo[3,2,1-ij]quinolin-4-one (30 mg; prepared according to WO 2010/041194) and the compound of Preparation D (40 mg), and proceeding in analogy to Example 1, the title compound was obtained, after purification by prep-HPLC (Method 1), as a colourless oil (36 mg; 54% yield).
MS1 (ESI, m/z): 467.1 [M+H⁺]; $t_R$=0.70 min.

Example 5

(R)-6-{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one Starting from (R)-6-amino-7-fluoro-5,6-di hydro-pyrrolo[1,2,3-de]quinoxalin-3-one (30 mg; prepared according to WO 2010/041194) and the compound of Preparation D (40 mg), and proceeding in analogy to Example 1, the title compound was obtained, after purification by prep-HPLC (Method 1), as an orange oil (33 mg; 49% yield).
MS1 (ESI, m/z): 468.2 [M+H⁺]; $t_R$=0.70 min.

Example 6

(R)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one Starting from (R)-6-amino-7-fluoro-5,6-di hydro-pyrrolo[1,2,3-de]quinoxalin-3-one (14 mg; prepared according to WO 2010/041194) and the compound of Preparation E (20 mg), and proceeding in analogy to Example 1, the title compound was obtained, after purification by prep-HPLC (Method 1), as an orange solid (5 mg; 15% yield).
MS3 (ESI, m/z): 480.2 [M+H⁺]; $t_R$=0.54 min.

Example 7

(S)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one Starting from (S)-6-amino-7-fluoro-5,6-dihydro-pyrrolo[1,2,3-de]quinoxalin-3-one (14 mg; prepared according to WO 2010/041194) and the compound of Preparation E (20 mg), and proceeding in analogy to Example 1, the title compound was obtained, after purification by prep-HPLC (Method 1), as an orange solid (8 mg; 25% yield).
MS3 (ESI, m/z): 480.2 [M+H⁺]; $t_R$=0.54 min.

Example 8

(S)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one Starting from (S)-1-amino-9-fluoro-1,2-dihydro-pyrrolo[3,2,1-ij]quinolin-4-one (39 mg, prepared according to WO 2010/041194) and the compound of Preparation E (56 mg), and proceeding in analogy to Example 1, the title compound was obtained, after purification by prep-HPLC (Method 1), as an orange solid (30 mg; 33% yield).
MS3 (ESI, m/z): 479.2 [M+H⁺]; $t_R$=0.55 min.

Example 9

(R)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one Starting from (R)-1-amino-9-fluoro-1,2-dihydro-pyrrolo[3,2,1-ij]quinolin-4-one (14 mg; prepared according to WO 2010/041194) and the compound of Preparation E (20 mg), and proceeding in analogy to Example 1, the title compound was obtained, after purification by prep-HPLC (Method 1), as an orange solid (16 mg; 48% yield).

MS3 (ESI, m/z): 479.2 [M+H$^+$]; $t_R$=0.55 min.

Example 10

(S)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one Starting from (S)-6-amino-7-fluoro-5,6-dihydro-pyrrolo[1,2,3-de]quinoxalin-3-one (14 mg; prepared according to WO 2010/041194) and the compound of Preparation F (33 mg), and proceeding in analogy to Example 1, the title compound was obtained, after purification by prep-HPLC (Method 1), as an off-white powder (10 mg; 30% yield).

MS3 (ESI, m/z): 479.1 [M+H$^+$]; $t_R$=0.57 min.

Example 11

(S)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one Starting from (S)-1-amino-9-fluoro-1,2-di hydro-pyrrolo[3,2,1-ij]quinolin-4-one (39 mg; prepared according to WO 2010/041194) and the compound of Preparation F (93 mg), and proceeding in analogy to Example 1, the title compound was obtained, after purification by prep-HPLC (Method 1), as an off-white powder (23 mg; 25% yield).

MS3 (ESI, m/z): 478.2 [M+H$^+$]; $t_R$=0.58 min.

Example 12

(R)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one Starting from (R)-1-amino-9-fluoro-1,2-dihydro-pyrrolo[3,2,1-ij]quinolin-4-one (14 mg; prepared according to WO 2010/041194) and the compound of Preparation F (33 mg), and proceeding in analogy to Example 1, the title compound was obtained, after purification by prep-HPLC (Method 1), as a colourless powder (10 mg; 30% yield).

MS3 (ESI, m/z): 478.1 [M+H$^+$]; $t_R$=0.58 min.

Example 13

(R)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one Starting from (R)-6-amino-7-fluoro-5,6-di hydro-pyrrolo[1,2,3-de]quinoxalin-3-one (14 mg; prepared according to WO 2010/041194) and the compound of Preparation F (33 mg), and proceeding in analogy to Example 1, the title compound was obtained, after purification by prep-HPLC (Method 1), as a colourless powder (11 mg; 34% yield).

MS3 (ESI, m/z): 479.1 [M+H$^+$]; $t_R$=0.57 min.

Example 14

(R)-9-fluoro-1-{3-[5-oxo-4-(3-oxo-3,4-dihydro-2H-pyrido[3,2-b][1,4]-thiazin-6-yl)-4,5-dihydro-[1,3,4]oxadiazol-2-yl]-propylamino}-1,2-dihydro-pyrrolo[3,2,1-ij]quinolin-4-one Starting from (R)-1-amino-9-fluoro-1,2-di hydro-pyrrolo[3,2,1-ij]quinolin-4-one (25 mg; prepared according to WO 2010/041194) and the compound of Preparation G (37 mg), and proceeding in analogy to Example 1, the title compound was obtained, after purification by prep-HPLC (Method 1), as an off-white powder (6 mg; 10% yield).

MS3 (ESI, m/z): 495.2 [M+H$^+$]; $t_R$=0.58 min.

Example 15

(S)-9-fluoro-1-{3-[5-oxo-4-(3-oxo-3,4-dihydro-2H-benzo[1,4]-thiazin-6-yl)-4,5-dihydro-[1,3,4]oxadiazol-2-yl]-propylamino}-1,2-dihydro-pyrrolo[3,2,1-ij]quinolin-4-one Starting from (S)-1-amino-9-fluoro-1,2-dihydro-pyrrolo[3,2,1-ij]quinolin-4-one (20 mg; prepared according to WO 2010/041194) and the compound of Preparation H (30 mg), and proceeding in analogy to Example 1, the title compound was obtained, after purification by prep-HPLC (Method 1), as an orange foam (20 mg; 41% yield).

MS1 (ESI, m/z): 494.3 [M+H$^+$]; $t_R$=0.60 min.

Example 16

(R)-7-fluoro-6-{3-[5-oxo-4-(3-oxo-3,4-dihydro-2H-pyrido[3,2-b][1,4]-thiazin-6-yl)-4,5-dihydro-[1,3,4]oxadiazol-2-yl]-propylamino}-5,6-dihydro-pyrrolo[1,2,3-de]quinoxalin-3-one Starting from (R)-6-amino-7-fluoro-5,6-dihydro-pyrrolo[1,2,3-de]quinoxalin-3-one (25 mg; prepared according to WO 2010/041194) and the compound of Preparation G (37 mg), and proceeding in analogy to Example 1 (Method 1), the title compound was obtained, after purification by prep-HPLC, as an off-white powder (5 mg; 9% yield).

MS3 (ESI, m/z): 496.2 [M+H$^+$]; $t_R$=0.57 min.

Example 17

(S)-9-fluoro-1-{3-[5-oxo-4-(3-oxo-3,4-dihydro-2H-pyrido[3,2-b][1,4]-thiazin-6-yl)-4,5-dihydro-[1,3,4]oxadiazol-2-yl]-propylamino}-1,2-dihydro-pyrrolo[3,2,1-ij]quinolin-4-one Starting from (S)-1-amino-9-fluoro-1,2-dihydro-pyrrolo[3,2,1-ij]quinolin-4-one (25 mg; prepared according to WO 2010/041194) and the compound of Preparation G (37 mg), and proceeding in analogy to Example 1, the title compound was obtained, after purification by prep-HPLC (Method 1), as an off-white foam (7 mg; 11% yield).

MS3 (ESI, m/z): 495.2 [M+H$^+$]; $t_R$=0.58 min.

Example 18

(S)-7-fluoro-6-{3-[5-oxo-4-(3-oxo-3,4-dihydro-2H-pyrido[3,2-b][1,4]-thiazin-6-yl)-4,5-dihydro-[1,3,4] oxadiazol-2-yl]-propylamino}-5,6-dihydro-pyrrolo [1,2,3-de]quinoxalin-3-one Starting from (S)-6-amino-7-fluoro-5,6-dihydro-pyrrolo [1,2,3-de]quinoxalin-3-one (25 mg; prepared according to WO 2010/041194) and the compound of Preparation G (38 mg), and proceeding in analogy to Example 1, the title compound was obtained, after purification by prep-HPLC (Method 1), as an off-white solid (7 mg; 11% yield).

MS3 (ESI, m/z): 496.2 [M+H$^+$]; $t_R$=0.57 min.

Example 19

(R)-9-fluoro-1-{3-[5-oxo-4-(3-oxo-3,4-dihydro-2H-benzo[1,4]-thiazin-6-yl)-4,5-dihydro-[1,3,4]oxadi-azol-2-yl]-propylamino}-1,2-dihydro-pyrrolo[3,2,1-ij]quinolin-4-one Starting from (R)-1-amino-9-fluoro-1,2-dihydro-pyrrolo [3,2,1-ij]quinolin-4-one (12 mg; prepared according to WO 2010/041194) and the compound of Preparation H (15 mg), and proceeding in analogy to Example 1, the title compound was obtained, after purification by prep-HPLC (Method 1), as a colourless powder (10 mg; 34% yield).

MS3 (ESI, m/z): 494.2 [M+H$^+$]; $t_R$=0.61 min.

Example 20

(S)-7-fluoro-6-{3-[5-oxo-4-(3-oxo-3,4-dihydro-2H-benzo[1,4]-thiazin-6-yl)-4,5-dihydro-[1,3,4]oxadi-azol-2-yl]-propylamino}-5,6-dihydro-pyrrolo[1,2,3-de]quinoxalin-3-one Starting from (S)-6-amino-7-fluoro-5,6-dihydro-pyrrolo [1,2,3-de]quinoxalin-3-one (12 mg; prepared according to WO 2010/041194) and the compound of Preparation H (15 mg), and proceeding in analogy to Example 1, the title compound was obtained, after purification by prep-HPLC (Method 1), as a colourless powder (5 mg; 17% yield).

MS3 (ESI, m/z): 495.2 [M+H$^+$]; $t_R$=0.60 min.

Example 21

(R)-7-fluoro-6-{3-[5-oxo-4-(3-oxo-3,4-dihydro-2H-benzo[1,4]-thiazin-6-yl)-4,5-dihydro-[1,3,4]oxadi-azol-2-yl]-propylamino}-5,6-dihydro-pyrrolo[1,2,3-de]quinoxalin-3-one Starting from (R)-6-amino-7-fluoro-5,6-dihydro-pyrrolo [1,2,3-de]quinoxalin-3-one (12 mg; prepared according to WO 2010/041194) and the compound of Preparation H (15 mg), and proceeding in analogy to Example 1, the title compound was obtained, after purification by prep-HPLC (Method 1), as a beige powder (4.5 mg; 16% yield).

MS3 (ESI, m/z): 495.2 [M+H$^+$]; $t_R$=0.60 min.

Example 22

(S)-1-{3-[4-(2,3-dihydro-benzo[1,4]dioxin-6-yl)-5-oxo-4,5-dihydro-[1,3,4]oxadiazol-2-yl]-propy-lamino}-9-fluoro-1,2-dihydro-pyrrolo[3,2,1-ij]quino-lin-4-one Starting from (S)-1-amino-9-fluoro-1,2-dihydro-pyrrolo [3,2,1-ij]quinolin-4-one (10 mg; prepared according to WO 2010/041194) and the compound of Preparation I (7 mg), and proceeding in analogy to Example 1, the title compound was obtained, after purification by prep-HPLC (Method 1), as a colourless powder (6 mg; 36% yield).

MS3 (ESI, m/z): 465.1 [M+H$^+$]; $t_R$=0.63 min.

Example 23

(R)-1-{3-[4-(2,3-dihydro-benzo[1,4]dioxin-6-yl)-5-oxo-4,5-dihydro-[1,3,4]oxadiazol-2-yl]-propy-lamino}-9-fluoro-1,2-dihydro-pyrrolo[3,2,1-ij]quino-lin-4-one Starting from (R)-1-amino-9-fluoro-1,2-dihydro-pyrrolo [3,2,1-ij]quinolin-4-one (10 mg; prepared according to WO 2010/041194) and the compound of Preparation I (7 mg), and proceeding in analogy to Example 1, the title compound was obtained, after purification by prep-HPLC (Method 1), as a colourless powder (8 mg; 48% yield).

MS3 (ESI, m/z): 465.1 [M+H$^+$]; $t_R$=0.63 min.

Example 24

(S)-6-{3-[4-(2,3-dihydro-benzo[1,4]dioxin-6-yl)-5-oxo-4,5-dihydro-[1,3,4]oxadiazol-2-yl]-propy-lamino}-7-fluoro-5,6-dihydro-pyrrolo[1,2,3-de]qui-noxalin-3-one Starting from (S)-6-amino-7-fluoro-5,6-dihydro-pyrrolo [1,2,3-de]quinoxalin-3-one (10 mg; prepared according to WO 2010/041194) and the compound of Preparation I (7 mg), and proceeding in analogy to Example 1, the title compound was obtained, after purification by prep-HPLC (Method 1), as a beige powder (9 mg; 53% yield).

MS3 (ESI, m/z): 466.1 [M+H$^+$]; $t_R$=0.62 min.

Example 25

(R)-6-{3-[4-(2,3-dihydro-benzo[1,4]dioxin-6-yl)-5-oxo-4,5-dihydro-[1,3,4]oxadiazol-2-yl]-propy-lamino}-7-fluoro-5,6-dihydro-pyrrolo[1,2,3-de]qui-noxalin-3-one Starting from (R)-6-amino-7-fluoro-5,6-dihydro-pyrrolo [1,2,3-de]quinoxalin-3-one (10 mg; prepared according to WO 2010/041194) and the compound of Preparation I (7 mg), and proceeding in analogy to Example 1, the title compound was obtained, after purification by prep-HPLC (Method 1), as a beige powder (7 mg; 42% yield).

MS3 (ESI, m/z): 466.1 [M+H$^+$]; $t_R$=0.62 min.

Example 26

(R)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one Starting from (R)-1-amino-9-fluoro-1,2-dihydro-pyrrolo [3,2,1-ij]quinolin-4-one (30 mg; prepared according to WO 2010/041194) and the compound of Preparation B (38 mg), and proceeding in analogy to Example 1, the title compound was obtained, after purification by prep-HPLC (Method 1), as an orange oil (21 mg; 32% yield).

MS3 (ESI, m/z): 449.4 [M+H$^+$]; $t_R$=0.72 min.

Example 27

(S)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one Starting from (S)-6-amino-7-fluoro-5,6-dihydro-pyrrolo[1,2,3-de]quinoxalin-3-one (30 mg; prepared according to WO 2010/041194) and the compound of Preparation B (38 mg), and proceeding in analogy to Example 1, the title compound was obtained, after purification by prep-HPLC (Method 1), as a yellow oil (25 mg; 38% yield).

MS3 (ESI, m/z): 450.3 [M+H$^+$]; $t_R$=0.71 min.

Example 28

(S)-1-{3-[4-(4-ethoxy-phenyl)-5-oxo-4,5-dihydro-[1,3,4]oxadiazol-2-yl]-propylamino}-9-fluoro-1,2-dihydro-pyrrolo[3,2,1-ij]quinolin-4-one Starting from (S)-1-amino-9-fluoro-1,2-dihydro-pyrrolo[3,2,1-ij]quinolin-4-one (12 mg; prepared according to WO 2010/041194) and the compound of Preparation J (15 mg), and proceeding in analogy to Example 1, the title compound was obtained, after purification by prep-HPLC (Method 1), as a light yellow oil (11 mg; 43% yield).

MS3 (ESI, m/z): 451.1 [M+H$^+$]; $t_R$=0.66 min.

Example 29

(R)-1-{3-[4-(4-ethoxy-phenyl)-5-oxo-4,5-dihydro-[1,3,4]oxadiazol-2-yl]-propylamino}-9-fluoro-1,2-dihydro-pyrrolo[3,2,1-ij]quinolin-4-one Starting from (R)-1-amino-9-fluoro-1,2-dihydro-pyrrolo[3,2,1-ij]quinolin-4-one (12 mg; prepared according to WO 2010/041194) and the compound of Preparation J (15 mg), and proceeding in analogy to Example 1, the title compound was obtained, after purification by prep-HPLC (Method 1), as a light yellow oil (14 mg; 54% yield).

MS3 (ESI, m/z): 451.2 [M+H$^+$]; $t_R$=0.66 min.

Example 30

(S)-6-{3-[4-(4-ethoxy-phenyl)-5-oxo-4,5-dihydro-[1,3,4]oxadiazol-2-yl]-propylamino}-7-fluoro-5,6-dihydro-pyrrolo[1,2,3-de]quinoxalin-3-one Starting from (S)-6-amino-7-fluoro-5,6-dihydro-pyrrolo[1,2,3-de]quinoxalin-3-one (12 mg; prepared according to WO 2010/041194) and the compound of Preparation J (15 mg), and proceeding in analogy to Example 1, the title compound was obtained, after purification by prep-HPLC (Method 1), as a light orange oil (11 mg; 43% yield).

MS3 (ESI, m/z): 452.1 [M+H$^+$]; $t_R$=0.65 min.

Example 31

(R)-6-{3-[4-(4-ethoxy-phenyl)-5-oxo-4,5-dihydro-[1,3,4]oxadiazol-2-yl]-propylamino}-7-fluoro-5,6-dihydro-pyrrolo[1,2,3-de]quinoxalin-3-one Starting from (R)-6-amino-7-fluoro-5,6-dihydro-pyrrolo[1,2,3-de]quinoxalin-3-one (12 mg; prepared according to WO 2010/041194) and the compound of Preparation J (15 mg), and proceeding in analogy to Example 1, the title compound was obtained, after purification by prep-HPLC (Method 1), as a light yellow oil (9 mg; 35% yield).

MS3 (ESI, m/z): 452.2 [M+H$^+$]; $t_R$=0.65 min.

Example 32

(R)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one Starting from (R)-1-amino-9-fluoro-1,2-dihydro-pyrrolo[3,2,1-ij]quinolin-4-one (7 mg; prepared according to WO 2010/041194) and the compound of Preparation D (9 mg), and proceeding in analogy to Example 1, the title compound was obtained, after purification by prep-HPLC (Method 1), as a light yellow oil (7 mg; 44% yield).

MS3 (ESI, m/z): 467.2 [M+H$^+$]; $t_R$=0.70 min.

Example 33

(S)-6-{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one Starting from (S)-6-amino-7-fluoro-5,6-dihydro-pyrrolo[1,2,3-de]quinoxalin-3-one (7 mg; prepared according to WO 2010/041194) and the compound of Preparation D (9 mg), and proceeding in analogy to Example 1, the title compound was obtained, after purification by prep-HPLC (Method 1), as a light yellow oil (6 mg; 38% yield).

MS3 (ESI, m/z): 468.2 [M+H$^+$]; $t_R$=0.69 min.

Example 34

(S)-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one Starting from (1S)-1-amino-1,2-dihydro-4H-pyrrolo[3,2,1-ij]quinolin-4-one (6.4 mg; prepared according to WO 2010/041194) and the compound of Preparation E (10 mg), and proceeding in analogy to Example 1, the title compound was obtained, without purification by prep-HPLC (Method 1) as a yellow solid (6 mg; 38% yield).

MS1 (ESI, m/z): 460.96 [M+H$^+$]; $t_R$=0.54 min.

Example 35

(S)-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one Starting from (6S)-6-amino-5,6-dihydro-3H-pyrrolo[1,2,3-de]quinoxalin-3-one (6.4 mg; prepared according to WO 2010/041194) and the compound of Preparation E (10 mg), and proceeding in analogy to Example 1, the title compound was obtained, after purification by prep-HPLC (Method 1), as an off-white solid (3 mg; 21% yield).

MS1 (ESI, m/z): 461.91 [M+H$^+$]; $t_R$=0.52 min.

Example 36

(R)-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one Starting from (6R)-6-amino-5,6-dihydro-3H-pyrrolo[1,2,3-de]quinoxalin-3-one (6.4 mg; prepared according to WO 2010/041194) and the compound of Preparation E (10 mg), and proceeding in analogy to Example 1, the title compound was obtained, after purification by prep-HPLC (Method 2), as an off-white solid (4.7 mg; 30% yield).

MS1 (ESI, m/z): 462.00 [M+H$^+$]; $t_R$=0.52 min.

Example 37

(S)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-4,5-dihydro-pyrrolo[3,2,1-de][1,5]naphthyridin-7-one Starting from (S)-4-amino-3-fluoro-4H-pyrrolo[3,2,1-de][1,5]naphthyridin-7(5H)-one (7 mg; prepared according to WO 2010/041194) and the compound of Preparation E (10 mg), and proceeding in analogy to Example 1, the title compound was obtained, after purification by prep-HPLC (Method 2), as a colourless solid (6 mg; 36% yield).

MS1 (ESI, m/z): 479.93 [M+H$^+$]; $t_R$=0.54 min.

Example 38

(R)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-4,5-dihydro-pyrrolo[3,2,1-de][1,5]naphthyridin-7-one Starting from (R)-4-amino-3-fluoro-4H-pyrrolo[3,2,1-de][1,5]naphthyridin-7(5H)-one (7 mg; prepared according to WO 2010/041194) and the compound of Preparation E (10 mg), and proceeding in analogy to Example 1, the title compound was obtained, after purification by prep-HPLC (Method 2), as a colourless solid (6 mg; 34% yield).

MS1 (ESI, m/z): 479.92 [M+H$^+$]; $t_R$=0.51 min.

Example 39

(S)-9-methoxy-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one Starting from compound of Preparation K (7.5 mg) and the compound of Preparation E (10 mg), and proceeding in analogy to Example 1, the title compound was obtained, after purification by prep-HPLC (Method 2), as an orange solid (4 mg; 26% yield).

MS1 (ESI, m/z): 490.97 [M+H$^+$]; $t_R$=0.56 min.

Example 40

(S)-9-methyl-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one Starting from compound of Preparation L (6.8 mg) and the compound of Preparation E (10 mg), and proceeding in analogy to Example 1, the title compound was obtained, after purification by prep-HPLC (Method 2), as a colourless solid (4 mg; 24% yield).

MS1 (ESI, m/z): 474.98 [M+H$^+$]; $t_R$=0.56 min.

Example 41

(S)-4-oxo-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-4H-pyrrolo[3,2,1-ij]quinoline-9-carbonitrile Starting from compound of preparation M (7.3 mg) and the compound of Preparation E (10 mg), and proceeding in analogy to Example 1, the title compound was obtained, after purification by prep-HPLC (Method 2), as a beige solid (8.2 mg; 49% yield).

$^1$H NMR (500 MHz, DMSO) δ: 11.49 (m, 1H); 8.01 (d, J=9.5 Hz, 1H); 7.77 (d, J=8.1 Hz, 1H); 7.54 (dd, J=8.1, 10.7 Hz, 2H); 7.31 (d, J=8.5 Hz, 1H); 6.76 (d, J=9.5 Hz); 6.76 (d, J=9.5 Hz, 1H); 4.93 (dd, J=3.5, 8.1 Hz, 1H); 4.68 (s, 2H); 4.41 (m, 1H); 4.16 (dd, J=3.6, 12.7 Hz, 1H); 2.81 (t, J=7.4 Hz, 2H); 2.73 (m, 2H); 2.55 (s, 1H); 1.82 (m, 2H).

MS1 (ESI, m/z): 485.96 [M+H$^+$]; $t_R$=0.55 min.

Pharmacological Properties of the Invention Compounds
In Vitro Assays
Bacterial Growth Minimal Inhibitory Concentrations:
Experimental Methods:

Minimal Inhibitory Concentrations (MICs; mg/L) were determined in cation-adjusted MuellerHinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

Results:

All Example compounds were tested against several Gram positive and Gram negative bacteria.

All Example compounds were tested against several Gram positive and Gram negative bacteria. Typical antibacterial test results are given in Table 1 hereafter (MICs in mg/l). *Staphylococcus aureus* A798, *Enterococcus faecium* A949 and *Acinetobacter baumanii* T6474 are multiply-resistant strains (in particular quinolone-resistant), while *Moraxella catarrhalis* A894 is a quinolone-sensitive strain and *Staphylococcus aureus* ATCC29213 is a methicillin-sensitive and quinolone-sensitive strain.

TABLE 1

| Example No. | MIC for S. aureus ATCC29213 | MIC for S. aureus A798 | MIC for E. faecium A949 | MIC for M. catarrhalis A894 | MIC for A. baumanii T6474 |
|---|---|---|---|---|---|
| 1 | 0.25 | 2 | 1 | 2 | >8 |
| 2 | 0.125 | 0.5 | 1 | 2 | >8 |
| 3 | 0.063 | 0.25 | 0.25 | 2 | >8 |
| 4 | 0.063 | 0.5 | 0.5 | 0.5 | 8 |
| 5 | 0.031 | 0.063 | 0.5 | 0.25 | 4 |
| 6 | 0.5 | 0.5 | 2 | 0.5 | 2 |
| 7 | 0.25 | 0.5 | 2 | 0.25 | 2 |
| 8 | 0.125 | 0.25 | 0.5 | 0.125 | 0.5 |
| 9 | 0.125 | 0.25 | 0.5 | 0.125 | 1 |
| 10 | 0.031 | 0.063 | 0.5 | ≤0.016 | 0.25 |
| 11 | 0.031 | 0.063 | 0.25 | ≤0.016 | 0.25 |
| 12 | 0.031 | 0.031 | 0.25 | ≤0.016 | 0.25 |
| 13 | 0.031 | 0.031 | 0.25 | ≤0.016 | 0.25 |
| 14 | ≤0.016 | 0.031 | 0.25 | 0.031 | 0.25 |
| 15 | ≤0.016 | ≤0.016 | 0.063 | ≤0.016 | 0.125 |

TABLE 1-continued

| Example No. | MIC for S. aureus ATCC29213 | MIC for S. aureus A798 | MIC for E. faecium A949 | MIC for M. catarrhalis A894 | MIC for A. baumanii T6474 |
| --- | --- | --- | --- | --- | --- |
| 16 | 0.063 | 0.063 | 0.25 | 0.063 | 0.25 |
| 17 | 0.031 | 0.063 | 0.25 | 0.031 | 0.25 |
| 18 | 0.031 | 0.063 | 0.25 | ≤0.016 | 0.25 |
| 19 | ≤0.016 | ≤0.016 | 0.25 | 0.031 | ≤0.016 |
| 20 | ≤0.016 | ≤0.016 | 0.25 | 0.063 | ≤0.016 |
| 21 | ≤0.016 | ≤0.016 | 0.25 | 0.063 | ≤0.016 |
| 22 | 4 | >8 | >8 | 4 | 8 |
| 23 | 4 | 8 | >8 | 4 | >8 |
| 24 | 2 | 8 | >8 | 4 | 4 |
| 25 | 2 | 4 | 8 | 8 | 8 |
| 26 | 0.125 | 0.5 | 0.5 | 0.5 | 2 |
| 27 | 0.5 | 2 | 2 | 4 | 4 |
| 28 | 2 | 4 | >8 | 8 | 4 |
| 29 | 2 | 4 | >8 | 8 | 4 |
| 30 | 1 | 4 | 8 | 8 | 4 |
| 31 | 1 | 4 | >8 | 8 | 8 |
| 32 | 0.063 | 0.25 | 0.5 | 0.5 | 0.5 |
| 33 | 0.031 | 0.25 | 0.5 | 0.5 | 0.25 |
| 34 | 2 | 4 | 8 | 1 | 4 |
| 35 | 0.5 | 1 | 4 | 0.5 | 2 |
| 36 | 4 | 4 | 8 | 2 | 4 |
| 37 | 0.25 | 0.25 | 4 | 0.125 | 2 |
| 38 | 0.5 | 0.5 | 4 | 0.5 | 2 |
| 39 | 1 | 2 | 8 | 1 | 1 |
| 40 | 1 | 2 | 2 | 0.5 | 2 |
| 41 | 0.063 | 0.125 | 0.5 | 0.063 | 0.125 |
| Cipro | 0.5 | >32 | >8 | ≤0.016 | >32 |

The invention claimed is:

1. A compound of formula I

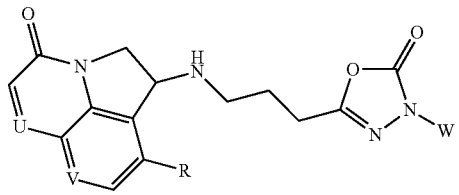

wherein

U represents CH or N;

V represents CH or N, provided that at least one of U and V does not represent N;

R represents H, halogen, methyl, methoxy, cyano or ethynyl;

either W represents a phenyl group substituted in para position with $(C_1-C_3)$alkyl, $(C_1-C_3)$alkoxy or $(C_1-C_3)$thioalkoxy and optionally in meta position with halogen, or W is a group having one of the formula $W^1$ or $W^2$ below;

$W^1$

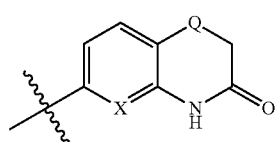

$W^2$ wherein

Q is O or S and

X is CH or N;

or a salt thereof.

2. The compound according to claim 1, wherein

V represents CH and

R represents fluorine;

or a salt thereof.

3. The compound according to claim 1, wherein U represents CH; or a salt thereof.

4. The compound according to claim 3, wherein W is a group of formula $W^1$ or a salt thereof.

5. The compound according to claim 1, wherein U represents N; or a salt thereof.

6. The compound according to claim 5, wherein W is a group of formula $W^1$ or a salt thereof.

7. The compound according to claim 1, wherein W represents a phenyl group substituted in para position with $(C_2-C_3)$alkyl, $(C_1-C_2)$alkoxy or $(C_1-C_2)$thioalkoxy and optionally in meta position with fluorine;

or a salt thereof.

8. The compound according to claim 1, wherein W is a group of formula $W^1$ or a salt thereof.

9. The compound according to claim 1, wherein W is a group of formula $W^2$ or a salt thereof.

10. The compound according to claim 1, wherein

R represents H, fluorine or cyano; and either W represents a phenyl group substituted in para position with $(C_2-C_3)$alkyl, $(C_1-C_2)$thioalkoxy or $(C_1-C_2)$alkoxy and optionally in meta position with fluorine, or W is a group having one of the formula $W^1$ or $W^2$ or a salt thereof.

11. The compound according to claim 1, wherein said compound is:

(S)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one;

(R)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one;

(S)-9-fluoro-1-{3-[4-(4-isopropyl-phenyl)-5-oxo-4,5-dihydro-[1,3,4]oxadiazol-2-yl]-propylamino}-1,2-dihydro-pyrrolo[3,2,1-ij]quinolin-4-one;

(S)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one;

(R)-6-{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;

(R)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;

(S)-7-fluoro-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
(R)-9-fluoro-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one;
(R)-9-fluoro-1-{3-[5-oxo-4-(3-oxo-3,4-dihydro-2H-benzo[1,4]oxazin-6-yl)-4,5-dihydro-[1,3,4]oxadiazol-2-yl]-propylamino}-1,2-dihydro-pyrrolo[3,2,1-ij]quinolin-4-one;
(R)-7-fluoro-6-{3-[5-oxo-4-(3-oxo-3,4-dihydro-2H-benzo[1,4]oxazin-6-yl)-4,5-dihydro-[1,3,4]oxadiazol-2-yl]-propylamino}-5,6-dihydro-pyrrolo[1,2,3-de]quinoxalin-3-one;
(R)-9-fluoro-1-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-1,2-dihydro-pyrrolo[3,2,1-ij]quinolin-4-one;
(S)-9-fluoro-1-{3-[5-oxo-4-(3-oxo-3,4-dihydro-2H-benzo[1,4]thiazin-6-yl)-4,5-dihydro-[1,3,4]oxadiazol-2-yl]-propylamino}-1,2-dihydro-pyrrolo[3,2,1-ij]quinolin-4-one;
(R)-7-fluoro-6-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-5,6-dihydro-pyrrolo[1,2,3-de]quinoxalin-3-one;
(S)-9-fluoro-1-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-pyrido[3,2-b][1,4]thiazin-6-yl)-4,5-dihydro-[1,3,4]oxadiazol-2-yl]-propylamino}-5,6-dihydro-pyrrolo[1,2,3-de]quinoxalin-3-one;
(R)-9-fluoro-1-{3-[5-oxo-4-(3-oxo-3,4-dihydro-2H-benzo[1,4]thiazin-6-yl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(3-oxo-3,4-dihydro-2H-benzo[1,4]thiazin-6-yl)-4,5-dihydro-[1,3,4]oxadiazol-2-yl]-propylamino}-5,6-dihydro-pyrrolo[1,2,3-de]quinoxalin-3-one;
(R)-7-fluoro-6-{3-[5-oxo-4-(3-oxo-3,4-dihydro-2H-benzo[1,4]thiazin-6-yl)-4,5-dihydro-[1,3,4]oxadiazol-2-yl]-propylamino}-5,6-dihydro-pyrrolo[1,2,3-de]quinoxalin-3-one;
(S)-1-{3-[4-(2,3-dihydro-benzo[1,4]dioxin-6-yl)-5-oxo-4,5-dihydro-[1,3,4]oxadiazol-2-yl]-propylamino}-9-fluoro-1,2-dihydro-pyrrolo[3,2,1-ij]quinolin-4-one;
(R)-1-{3-[4-(2,3-dihydro-benzo[1,4]dioxin-6-yl)-5-oxo-4,5-dihydro-[1,3,4]oxadiazol-2-yl]-propylamino}-9-fluoro-1,2-dihydro-pyrrolo[3,2,1-ij]quinolin-4-one;
(S)-6-{3-[4-(2,3-dihydro-benzo[1,4]dioxin-6-yl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-6-{3-[4-(2,3-dihydro-benzo[1,4]dioxin-6-yl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-9-fluoro-1-{3-[5-oxo-4-(4-propyl-phenyl)-4,5-dihydro-[1,3,4]oxadiazol-2-yl]-propylamino}-1,2-dihydro-pyrrolo[3,2,1-ij]quinolin-4-one;
(S)-7-fluoro-6-{3-[5-oxo-4-(4-propyl-phenyl)-4,5-dihydro-[1,3,4]oxadiazol-2-yl]-propylamino}-5,6-dihydro-pyrrolo[1,2,3-de]quinoxalin-3-one;
(S)-1-{3-[4-(4-ethoxy-phenyl)-5-oxo-4,5-dihydro-[1,3,4]oxadiazol-2-yl]-propylamino}-9-fluoro-1,2-dihydro-pyrrolo[3,2,1-ij]quinolin-4-one;
(R)-1-{3-[4-(4-ethoxy-phenyl)-5-oxo-4,5-dihydro[1,3,4]oxadiazol-2-yl]-propylamino}-9-fluoro-1,2-dihydro-pyrrolo[3,2,1-ij]quinolin-4-one;
(S)-6-{3-[4-(4-ethoxy-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-6-{3-[4-(4-ethoxy-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;
(R)-1-{3-[4-(4-ethylsulfanyl-phenyl)-5-oxo-4,5-dihydro-[1,3,4]oxadiazol-2-yl]-propylamino}-9-fluoro-1,2-dihydro-pyrrolo[3,2,1-ij]quinolin-4-one;
{3-[4-(4-ethylsulfanyl-phenyl)-5-oxo-4,5-dihydro-[1,3,4]oxadiazol-2-yl]-propylamino}-7-fluoro-5,6-dihydro-pyrrolo[1,2,3-de]quinoxalin-3-one;
(S)-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;
(R)-6-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-5,6-dihydro-pyrrolo[1,2,3-de]quinoxalin-3-one;
(S)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-4,5-dihydro-pyrrolo[3,2,1-de][1,5]naphthyridin-7-one;
(R)-3-fluoro-4-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-4,5-dihydro-pyrrolo[3,2,1-de][1,5]naphthyridin-7-one;
(S)-9-methoxy-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one;
(S)-9-methyl-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-pyrrolo[3,2,1-ij]quinolin-4-one; or
(S)-4-oxo-1-{3-[5-oxo-4-(3-oxo-3,4-dihydro-2H-pyrido[3,2-b][1,4]oxazin-6-yl)-4,5-dihydro-[1,3,4]oxadiazol-2-yl]-propylamino}-1,2-dihydro-4H-pyrrolo[3,2,1-ij]quinoline-9-carbonitrile;
or a salt thereof.

12. A pharmaceutical composition comprising, as active principle, a compound according to claim 1, or a pharmaceutically acceptable salt thereof, and at least one therapeutically inert excipient.

13. A method of treating or preventing a bacterial infection comprising administering to a subject in need thereof an amount of the compound or a salt thereof according to claim 1.

14. The method according to claim 13 wherein the bacterial infection is respiratory tract infections, otitis media, meningitis, skin and soft tissue infections, pneumonia, bacteremia, endocarditis, intraabdominal infections, gastrointestinal infections, *Clostridium difficile* infections, urinary tract infections, sexually transmitted infections, foreign body infections, osteomyelitis, Lyme disease, topical infections, opthalmological infections, tuberculosis or tropical diseases.

15. A method of treating or preventing a bacterial infection mediated by *Staphylococcus aureus* bacteria or *Acinetobacter baumanii* bacteria comprising administering an amount of the composition or a salt thereof according to claim 12 to a subject in need thereof.

16. A method of treating or preventing a bacterial infection mediated by *Staphylococcus aureus* bacteria or *Acinetobacter baumanii* bacteria comprising administering to a subject in need thereof an amount of the compound or a salt thereof according to claim 1.

* * * * *